United States Patent [19]

Fässler et al.

[11] Patent Number: 5,912,352
[45] Date of Patent: Jun. 15, 1999

[54] INTERMEDIATES FOR THE PREPARATION OF PEPTIDE ANALOGUES

[75] Inventors: Alexander Fässler, Macclesfield, United Kingdom; Guido Bold, Gipf-Oberfrick, Switzerland; Hans-Georg Capraro, Rheinfelden, Switzerland; Heinz Steiner, Münchenstein, Switzerland

[73] Assignee: Novartis Finance Corporation, New York, N.Y.

[21] Appl. No.: 08/866,558

[22] Filed: May 30, 1997

[30] Foreign Application Priority Data

May 31, 1996 [CH] Switzerland .............................. 1366/96
Aug. 15, 1996 [CH] Switzerland .............................. 2007/96
Nov. 19, 1996 [CH] Switzerland .............................. 2850/96

[51] Int. Cl.⁶ ................................................. C07D 213/02
[52] U.S. Cl. ..................... 546/332; 564/148; 564/149; 564/151; 564/310
[58] Field of Search ................... 546/332; 564/148, 564/149, 151, 310

[56] References Cited

U.S. PATENT DOCUMENTS

| | | | |
|---|---|---|---|
| 4,599,198 | 7/1986 | Hoover et al. | 260/998.2 |
| 4,895,943 | 1/1990 | Friedman et al. | 540/556 |

FOREIGN PATENT DOCUMENTS

| | | |
|---|---|---|
| 0097617 | 1/1984 | European Pat. Off. |
| 0244083 | 11/1987 | European Pat. Off. |
| 0252727 | 1/1988 | European Pat. Off. |
| 0468641 | 1/1992 | European Pat. Off. |
| 0521827 | 1/1993 | European Pat. Off. |
| 0613895 | 9/1994 | European Pat. Off. |
| 1041982 | 9/1996 | United Kingdom . |
| 93/18006 | 9/1993 | WIPO . |
| 94/19332 | 9/1994 | WIPO . |
| 95/07269 | 3/1995 | WIPO . |
| 96/16079 | 5/1996 | WIPO . |
| 96/16080 | 5/1996 | WIPO . |
| 97/19055 | 5/1997 | WIPO . |

OTHER PUBLICATIONS

Sarantakis et al, Peptides 1992, Proc. Eur. Pept. Symp. 22nd, ESCOM, Leiden (NL), 1993, pp. 944–946.
Bonnat et al, Synthetic Communications, vol. 21: (1991) 1579–1582.
Brown et al, The Journal of Organic Chemistry, vol. 45:(1), (1980), pp. 1–12.
John M. McIntosh, Can. J. Chem. vol. 55, (1977), pp. 4200–4206.
Robl et al, Bioorganic & Medical Chemistry Letters, vol. 4, No. 16, (1994) pp. 2055–2060.
Attwood et al, Journal Chem. Soc. Perkin 1, (1986), pp. 1011–1018.
Fisher et al, Tetrahedron Letters, vol. 33, (1992), pp. 4533–4536.
Yoneda et al, Synthesis, (1986) pp. 1054–1055.
Matsubara et al, Chemistry Letters, vol. 8, (1991) pp. 1447–1450.
Harada et al, Chem. Pharm. Bull, vol. 37(9), (1989) pp. 2570–2572.
Matsuda et al, Chemistry Letters, vol. 5, (1990), pp. 723–724.
Herranz et al, Synthesis, vol. 9, (1989), pp. 703–705.
Wakamatsu et al, Heterocycles, vol. 14, (1980), P1437.
Rutjes et al, Tetrahedron Letters, vol. 49, (38), (1993), pp. 8605–8628.
Luly et al, J. Organic Chemistry, vol. 53, (1988), pp. 6109–6112.
Parris et al, Biochemistry, vol. 31 (35), (1992) pp. 8125–8141.
Gu et al, Chemistry Letters, vol. 7, (1992), pp. 1169–1172.
Beau et al, Carbohydrate Research, vol. 65, (1978) pp. 1–10.
Reetz et al, Tetrahedron Letters, vol. 29 (27) (1988), pp. 3295–3298.
Matsuda et al, Bull. Chem. Society Jpn. vol. 65, No. 2, (1992) pp. 360–365.

*Primary Examiner*—Zinna Northington Davis
*Attorney, Agent, or Firm*—Gregory D. Ferraro

[57] ABSTRACT

The invention relates to a novel process for the preparation of compounds of formula I

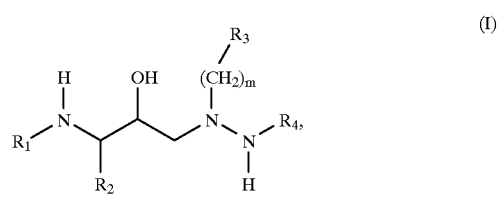

wherein $R_1$ is hydrogen or a suitable amino-protecting group, $R_2$ is unsubstituted or substituted alkyl, $R_3$ is hydrogen, aryl, heterocyclyl, unsubstituted or substituted alkyl or unsubstituted or substituted cycloalkyl, $R_4$, independently of $R_1$, is hydrogen or a suitable amino-protecting group and m is a number from 1 to 7; and wherein further suitable protecting groups for functional groups may be present; which compounds are antivirally active or can be used as starting materials for pharmaceutically active, especially antiviral compounds.

The precursor is an oxo compound,
which is in turn prepared by hydrogenation with a suitable complex hydride or with hydrogen in the presence of a suitable catalyst and acyl migration starting from a hydrazone,
which is in turn preferably prepared from a nitrile via an imino compound by means of hydrogenation and reaction with a hydrazine derivative,
which is prepared from an aldehyde by reaction with a reactive derivative of a carboxylic acid in the presence of a cyanide salt;
and the novel intermediates required therefor.

6 Claims, No Drawings

INTERMEDIATES FOR THE PREPARATION OF PEPTIDE ANALOGUES

BACKGROUND OF THE INVENTION

1. Field of the Invention

The present invention relates to a novel process for the preparation of 2,5-[diamino]-4-hydroxy-azahexane derivatives and to novel intermediates for the preparation thereof. The 2,5-[diamino]-4-hydroxy-azahexane derivatives serve as starting materials in the preparation of antiviral compounds or themselves exhibit antiviral activity.

2. Reference to the Prior Art

The present invention relates to the preparation of starting materials with a view to the preparation of end products of the 2,5-[diamino]-4-hydroxy-azahexane type that are suitable for the treatment of viral diseases, for example retroviral diseases, such as AIDS. Such antiviral end products are to be found, for example, in European Patent Applications EP 0 521 827 and EP 0 604 368 and in PCT Applications WO 93/18006, WO 95/07269 and WO 94/19332, those Applications also mention the test systems that enable the antiviral activity of the antiviral end products to be checked. Some of the starting materials also exhibit the pharmaceutical action mentioned.

The aim of the present invention is to provide an entirely novel process for the preparation of starting materials for the preparation of such compounds and to provide novel intermediates for that purpose.

The principal aims include to use simple starting materials, to avoid extreme reaction conditions, for example low-temperature reactions, to avoid intermediates that are difficult to prepare or handle (especially on a large scale), such as epoxides or Grignard reagents, to provide a novel method of obtaining the starting materials for the antiviral end products and/or especially to allow reaction steps to be carried out stereoselectively.

As a result of the novel reaction route described below, which yields the starting materials for the antiviral pharmaceutical active ingredients in a surprising manner, for example by means of a surprising acyl migration at a certain reaction step, one or more of the mentioned aims are unexpectedly achieved and also individual stereoisomers of compounds of formula I can be prepared in pure form and on a large scale, one advantage of the reaction route being a high degree of safeguarding against racemisation.

The intermediates of formula I can be utilised directly as pharmaceutically active compounds or can be converted into pharmaceutically active compounds by removal of protecting groups and acylation of radicals carrying $R_1$ and/or $R_4$ as protecting groups and, if necessary, further reactions, for example as described in European Patent Applications EP 0 521 827 and EP 0 604 368 and in PCT Applications WO 93/18006, WO 95/07269 and WO 94/19332, or in an analogous manner.

SUMMARY OF THE INVENTION

The present invention relates to a process for the preparation of compounds of formula I

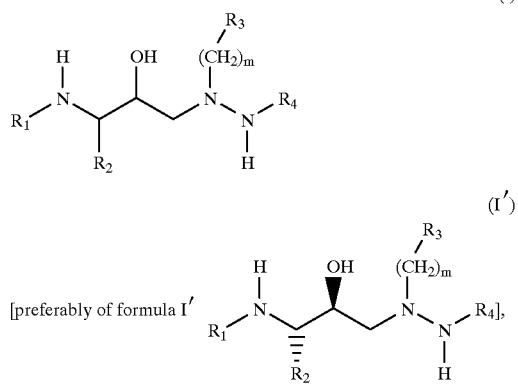

wherein
- $R_1$ is hydrogen or a suitable amino-protecting group,
- $R_2$ is unsubstituted or substituted alkyl,
- $R_3$ is hydrogen, aryl, heterocyclyl, unsubstituted or substituted alkyl or unsubstituted or substituted cycloalkyl,
- $R_4$, independently of $R_1$, is hydrogen or a suitable amino-protecting group and
- m is a number from 1 to 7;

and wherein further suitable protecting groups for functional groups that are not to participate in the reaction may be present;

or of salts thereof where salt-forming groups are present;

wherein the preparation is carried out by reduction of an oxo compound of formula II

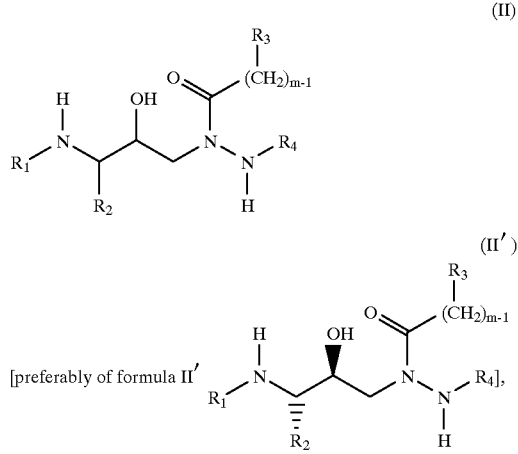

wherein $R_1$, $R_2$, $R_3$, $R_4$ and m are as defined for compounds of formula I, and wherein further suitable protecting groups for functional groups that are not to participate in the reaction may be present;

it being possible to introduce or remove protecting groups at suitable points in time;

which compound is in turn prepared by hydrogenation with a suitable complex hydride or with hydrogen in the presence of a suitable catalyst and acyl migration starting from a hydrazone of formula III

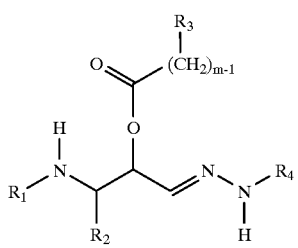
(III)

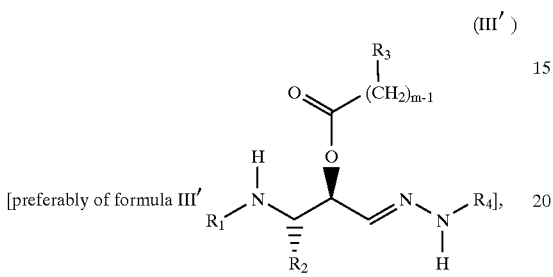
[preferably of formula III'] (III')

wherein $R_1$, $R_2$, $R_3$, $R_4$ and m are as defined for compounds of formula I, and wherein further suitable protecting groups for functional groups that are not to participate in the reaction may be present;

which compound is in turn obtained preferably from a nitrile of formula IV

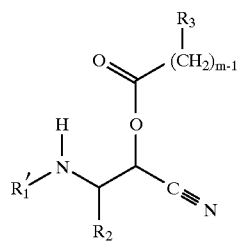
(IV)

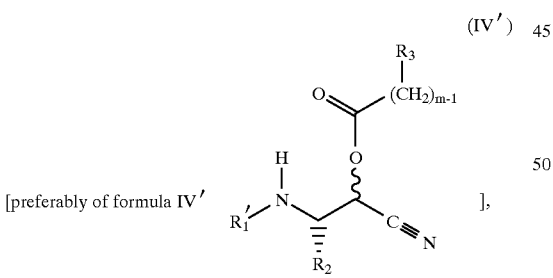
[preferably of formula IV'] (IV')

wherein $R_1{'}$ is an amino-protecting group and $R_2$, R 3 and m are as defined for compounds of formula I, by means of selective catalytic hydrogenation ((preferably) via an imino compound of formula V

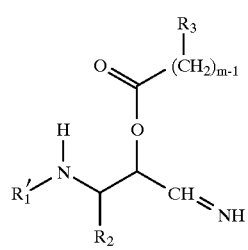
(V)

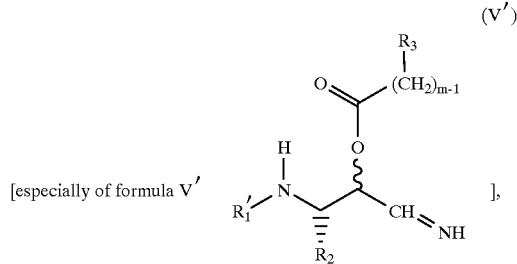
[especially of formula V'] (V')

wherein $R_1{'}$ is an amino-protecting group and $R_2$, $R_3$ and m are as defined for compounds of formula I and wherein further suitable protecting groups for functional groups that are not to participate in the reaction may be present) and reaction with a hydrazine derivative of formula VI

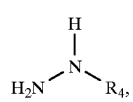
(VI)

wherein $R_4$ is as defined for a compound of formula I, and wherein further suitable protecting groups for functional groups that are not to participate in the reaction may be present;

the hydrazine derivative being added during the selective catalytic hydrogenation (or (further) being reacted with the resulting imino compound of formula V only when the catalytic hydrogenation is complete), the compound of formula IV being prepared preferably from an aldehyde of formula VII

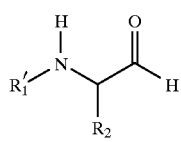
(VII)

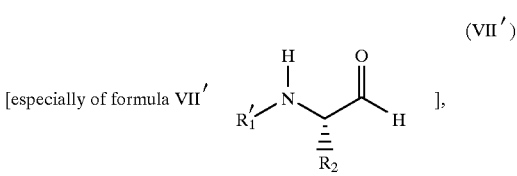
[especially of formula VII'] (VII')

wherein $R_1'$ is an amino-protecting group, and wherein further suitable protecting groups for functional groups that are not to participate in the reaction may be present;

by reaction with a reactive derivative of a carboxylic acid of formula VIII

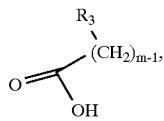

(VIII)

wherein $R_3$ and m are as defined for compounds of formula I, and wherein further suitable protecting groups for functional groups that are not to participate in the reaction may be present;

in the presence of a cyanide salt;

it being possible for the compounds of formulae II to VIII (preferably II' to VIII') to be used in free form or, where salt-forming groups are present, in the form of their salts;

and to the novel intermediates required therefor.

The compounds of formula I, especially of formula I', are antivirally active or are suitable for the preparation of antivirally active compounds.

Within the scope of this disclosure, unless indicated to the contrary, the general terms used hereinabove and hereinbelow preferably have the following meanings:

The term "lower" indicates a radical having up to and including a maximum of 7 carbon atoms, preferably up to and including a maximum of 4 carbon atoms, the radicals in question being unbranched or branched one or more times.

Lower alkyl is especially tert-butyl, sec-butyl, isobutyl, n-butyl, isopropyl, n-propyl, ethyl or methyl.

Any reference to compounds, salts and the like in the plural in a broader sense includes a compound, a salt and the like insofar as that does not contradict the disclosure.

Wherever references to publications, patents and patent applications are mentioned hereinabove and hereinbelow, those documents are considered to be incorporated by reference.

Hereinabove and hereinbelow the radicals $R_1$, $R_1'$, $R_2$, $R_3$ and $R_4$ and the index m each have the meanings that have been given above for the relevant formulae, unless indicated to the contrary.

Any asymmetric carbon atoms present, for example the carbon atoms bonded to the radicals $R_2$ and $R_3$—$(CH_2)_m$— or $R_3$—$(CH_2)_{m-1}$—C(=O)—, may be in the (R)—, (S—) or (R,S)—configuration, preferably in the (R)— or (S)-configuration, at least predominantly (that is to say 75% or more of one of the forms being present), with special preference being given to the (S)-configuration in the case of the carbon atoms carrying the two radicals in a compound of formula I and to corresponding configurations in the respective starting compounds. Accordingly the compounds of formulae I to VIII may be in the form of isomeric mixtures or in the form of pure isomers, preferably in the form of enantiomers or in the form of enantiomerically pure diastereoisomers.

A suitable amino-protecting group is especially an amino-protecting group that is not removed in any of the reductions and/or hydrogenations to be carried out in the reactions described hereinabove and hereinbelow. Also permissible, however, are protecting groups that are removable by those reductions, it being possible, if necessary, for fresh protecting groups to be introduced by conventional methods at each reaction step.

Suitable amino-protecting groups (conventional protecting groups) are those that are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis and the like. In certain cases the protecting groups can additionally cause reactions to proceed selectively, for example stereo-selectively. It is characteristic of protecting groups that they can be removed easily, i.e. without undesired secondary reactions taking place, for example by solvolysis, photolysis, or also enzymatically, for example also under physiological conditions; or also by means of reduction, in which case it will be necessary after one of the reductions and/or hydrogenations mentioned hereinabove and hereinbelow to re-introduce functional groups if required for further reactions. The person skilled in the art will know or can readily find out which amino-protecting groups are stable in the reductions and/or hydrogenations mentioned hereinabove and hereinbelow.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie"("Methods of Organic Chemistry"), Houben-Weyl, 4th edition, Volume 15/I, Georg Thieme Verlag, Stuttgart 1974, in H. -D. Jakubke and H. Jescheit, "Aminosäuren, Peptide, Proteine"("Amino acids, peptides, proteins"), Verlag Chemie, Weinheim, Deerfield Beach and Basle 1982, and in Jochen Lehmann, "Chemie der Kohlenhydrate: Monosaccharide und Derivate"("The Chemistry of Carbohydrates: monosaccharides and derivatives"), Georg Thieme Verlag, Stuttgart 1974.

Suitable amino-protecting groups are especially selected from unsubstituted or substituted alkyloxycarbonyl, alkenyloxycarbonyl, aryloxycarbonyl, aryl-lower alkoxycarbonyl, cyclo-alkyloxycarbonyl, unsubstituted or substituted bicycloalkyl-lower alkoxycarbonyl, tricycloalkyl-lower alkoxycarbonyl, heterocyclyloxycarbonyl, heterocyclyl-lower alkoxycarbonyl, substituted cycloalkenyl and alkylaminocarbonyl wherein the amino group is unsubstituted or substituted.

Alkyl in alkyloxycarbonyl has especially from 1 to 12 carbon atoms and is unbranched or, preferably, branched; preference is given to lower alkyl, such as methyl or ethyl, especially tert-lower alkyl, such as tert-butoxycarbonyl or tert-amyloxycarbonyl. Substituted alkyl in alkyloxycarbonyl contains one or more (preferably from 1 to 3) substituent(s), such as halogen, especially chlorine or iodine, lower alkanesulfonyl, such as methanesulfonyl, lower alkylphenyl-sulfonyl, such as 4-toluenesulfonyl, or cyano, and is especially 2-iodoethoxycarbonyl, 2,2,2-trichloro-tert-butoxycarbonyl, 2-methanesulfonyl-ethoxycarbonyl, 2-(4-toluenesulfonyl)-ethoxycarbonyl or preferably 2-cyano-tert-butoxycarbonyl.

Alkyloxycarbonyl is especially tert-lower alkoxycarbonyl, such as tert-butoxycarbonyl.

Alkenyl is especially alkenyl having from 1 to 12 carbon atoms, the double bond of which does not originate from the carbon atom bonding to the remainder of the molecule, and is especially lower alkenyl having the double bond in the 2-position, such as allyl.

Alkenyloxycarbonyl is especially lower alk-2-enyloxycarbonyl, such as allyloxycarbonyl.

Aryl in aryloxycarbonyl or aryl-lower alkoxycarbonyl has preferably from 6 to 14 carbon atoms, as in phenyl, naphthyl or fluorenyl, and is unsubstituted or substituted by one or more (preferably up to 3, especially 2 or more especially one) substituent(s) selected from halogen, such as fluorine or chlorine, nitro, cyano, phenylazo, lower alkoxy, such as methoxy, hydroxy, phenyl, cyanophenyl, such as 2-cyanophenyl, and heterocyclyl, wherein heterocyclyl is as defined hereinbelow, especially pyridyl, such as 2-pyridyl.

Aryl-lower alkoxycarbonyl is especially α,α-dimethyl-3,5-dimethoxy-benzyloxycarbonyl, 2-(4-biphenylyl)-propyl-2-oxycarbonyl or α-methyl-2,4,5-trimethylbenzyloxycarbonyl, in a border sense also benzyloxycarbonyl, 4-phenylazo-benzyloxycarbonyl, 2-, 3- or 4-nitro-benzyloxy-carbonyl, 2-, 3- or 4-chlorobenzyloxycarbonyl, 4-methoxybenzyloxycarbonyl, 4-phenyl-azobenzyloxycarbonyl, 4-cyanobenzyloxycarbonyl, 3,5-dimethoxy-benzyloxycarbonyl, 6nitroveratryloxycarbonyl or fluoren-9-yl-methoxycarbonyl.

The mentioned radicals aryloxycarbonyl and aryl-lower alkoxycarbonyl, especially aryloxy-carbonyl, are preferably not included in the group of suitable amino-protecting groups.

Cycloalkyl is especially $C_3$–$C_8$cycloalkyl, more especially cyclopentyl.

Cycloalkyloxycarbonyl is preferably $C_3$–$C_8$cycloalkyloxycarbonyl, such as cyclopentyloxycarbonyl.

Unsubstituted or substituted bicycloalkyl-lower alkyloxycarbonyl is especially $C_6$–$C_8$bicyclo-alkyl-methoxycarbonyl, such as isobornyloxycarbonyl, that is unsubstituted or substituted by one or two lower alkyl radicals, such as methyl.

Tricycloalkyl-lower alkoxycarbonyl is especially $C_6$–$C_{12}$tricycloalkyl-propyloxycarbonyl, such as 1-[1-adamantyl]-1-methyl-ethoxycarbonyl.

Heterocyclyl is especially a 3- or 4-membered ring having a hetero atom selected from oxygen, nitrogen and sulfur, or a 5- to 7-membered ring having one, two, three or four hetero atom(s) selected from oxygen, nitrogen and sulfur. A 5-membered ring may contain 0, 1 or 2 double bonds; a 6- or 7-membered ring may contain 0, 1, 2 or 3 double bonds. The ring nitrogen atoms may optionally be present in the form of tertiary or quaternised nitrogen (for example with lower alkyl) or be N-oxidised; sulfur atoms may optionally be oxidised with 1 or 2 oxygen atoms. Heterocyclyl includes also bicyclic radicals wherein each of the afore-mentioned rings is fused to a benzene, cyclopentane or cyclohexane ring or to one of the afore-mentioned simple heterocycles. Heterocyclyl is preferably pyrrolyl, pyrrolinyl, pyrrolidinyl, pyrazolyl, pyrazolinyl, pyrazolidinyl, imidazolyl, imidazolinyl, imidazolidinyl, tetrazolyl, pyridyl, piperidinyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, tetrahydroquinolinyl, isoquinolinyl, benzimidazolyl, benzothiazolyl, benzoxazolyl, benzofuranyl, furyl, dihydrofuranyl, tetrahydrofuranyl, pyranyl, dihydropyranyl, tetrahydropyranyl, dioxanyl, dioxolanyl, thienyl or benzothienyl. Preferred heterocycles are pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl. Heterocyclyl is unsubstituted or substituted, for example by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl. Special preference is given to unsubstituted pyridyl, piperidyl, oxazolyl, isoxazolyl, benzisoxazolyl, furanyl, tetrahydrofuranyl or tetrahydro[2H]-pyranyl and methyltetrazolyl.

Halogen is especially fluorine, chlorine, bromine or iodine, more especially fluorine or chlorine.

In heterocyclyloxycarbonyl, heterocyclyl is especially one of the radicals defined for heterocyclyl. Heterocyclyloxycarbonyl is especially piperidinooxycarbonyl or more especially benzisoxazolyloxycarbonyl. Heterocyclyloxycarbonyl protecting groups are among the less preferred protecting groups.

In heterocyclyl-lower alkoxycarbonyl, heterocyclyl is preferably one of the radicals defined for heterocyclyl. Preference is given to heterocyclylmethyloxycarbonyl, such as pyridylmethyloxycarbonyl, especially 4-pyridylmethoxycarbonyl, piperidylmethyloxycarbonyl, thiazolylmethyloxycarbonyl, isothiazolylmethyloxycarbonyl, oxazolylmethyloxycarbonyl, isoxazolylmethyloxycarbonyl, benzisoxazolylmethyloxycarbonyl, furanylmethyloxycarbonyl, such as furan-2-ylmethoxycarbonyl, thienylmethyloxycarbonyl, imidazolylmethyloxycarbonyl, pyrrolylmethyloxycarbonyl, tetrahydrofuranylmethyloxycarbonyl, tetrahydrothienylmethyloxycarbonyl and tetrahydro[2H]pyranylmethyloxycarbonyl, more especially pyridylmethyloxycarbonyl, piperidylmethyloxycarbonyl, oxazolylmethyloxycarbonyl, isoxazolylmethyloxycarbonyl, benzisoxazolylmethyloxycarbonyl, furanylmethyloxycarbonyl, such as furan-2-yl-methoxycarbonyl, imidazolylmethyloxycarbonyl, pyrrolylmethyloxycarbonyl, tetrahydrofuranylmethyloxycarbonyl and tetrahydro[2H]pyranylmethyloxycarbonyl.

Substituted cycloalkenyl is especially $C_3$–$C_8$cycloalkenyl that is substituted by up to three radicals selected from oxo and lower alkyl, such as methyl, and is especially 5,5-dimethyl-3-oxo-cyclohexen-1-yl.

Alkylaminocarbonyl, wherein the amino group is unsubstituted or substituted, is especially lower alkylaminocarbonyl, such as methylaminocarbonyl or ethylaminocarbonyl. Suitable amino substituents are especially lower alkyl and cycloalkyl.

Protecting groups that are not removable in any of the reductions and/or hydrogenations to be carried out in the reaction sequences mentioned hereinabove are especially 1-[1-adamantyl]-1-methylethoxycarbonyl, isobornyloxycarbonyl, cyclopentyloxycarbonyl, 5,5-dimethyl-3-oxo-cyclohexen-1-yl and more especially tert-lower alkoxycarbonyl, such as tertamyloxycarbonyl and especially tert-butoxycarbonyl. Very special preference is given to tert-butoxycarbonyl.

Further suitable protecting groups are, for example, N-benzyl and N,N-dibenzyl.

Unsubstituted or substituted alkyl $R_2$ is especially lower alkyl, more especially methyl, that is unsubstituted or preferably substituted by aryl, heterocyclyl or in a broader sense also by unsubstituted or substituted cycloalkyl. Special preference is given to phenylmethyl.

Aryl has preferably from 6 to 14 carbon atoms, as in phenyl, naphthyl or fluorenyl, and is unsubstituted or substituted by one or more (preferably up to 3, especially 2 or more especially one) substituent(s) selected from halogen, such as fluorine or chlorine, nitro, cyano, lower alkoxy, such as methoxy, hydroxy, phenyl, cyanophenyl, such as 2-cyanophenyl, and heterocyclyl, wherein heterocyclyl is as defined hereinabove and is especially pyridyl, such as 2-pyridyl.

Heterocyclyl is as defined hereinabove.

Unsubstituted or substituted cycloalkyl is especially $C_3$–$C_8$cycloalkyl that is substituted by one or more (preferably up to 3, especially 2 or more especially one) substituent(s) selected from halogen, such as fluorine or chlorine, nitro, cyano, lower alkoxy, such as methoxy, hydroxy, phenyl, cyanophenyl, such as 2-cyanophenyl, and heterocyclyl, wherein heterocyclyl is as defined hereinabove, especially pyridyl, such as 2-pyridyl. Special preference is given to cyclohexyl.

Unsubstituted or substituted alkyl $R_2$ is especially benzyl (phenylmethyl) or cyclohexylmethyl.

$R_3$ is preferably unsubstituted cycloalkyl, as defined hereinabove, or especially aryl.

Aryl $R_3$ is preferably defined in the same manner as aryl and is especially phenyl, 4-biphenylyl or 4-(pyridyl)-phenyl, such as 4-(pyridin-2-yl)phenyl.

The index m is preferably a number from 1 to 4, especially 1 or 2, more especially 1.

Salt-forming groups are basic groups, such as amino, or negatively charged groups, such as carboxy. Salts are formed, for example, by compounds having a basic nitrogen atom as acid addition salts. Further salts may be present if basic heterocyclyl radicals, such as pyridyl, are present. The salts include acid addition salts formed with organic or inorganic acids. Suitable inorganic acids are, for example, hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucose-monocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetocybenzoic acid, 4-aminosalicylic acid, phthalic acid, phenylacetic acid, mandelic acid, cinnamic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, and other organic protonic acids, such as ascorbic acid.

When negatively charged radicals are present, salts may be formed also with bases, for example metal or ammonium salts, such as alkali metal or alkaline earth metal salts, for example sodium, potassium, magnesium or calcium salts or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

The reduction of an oxo compound of formula II is preferably carried out using complex hydrides, such as a borohydride or metal hydride, especially using borane/tetrahydrofuran ($BH_3$/THF) (especially preferred), borane/dimethyl sulfide ($BH_3/(CH_3)_2S$), tetra(n-butyl)-ammonium borohydride (($CH_3$—$CH_2$—$CH_2$—$CH_2$—)$NBH_4$), a trialkoxyborohydride, such as tri-lower alkoxyborohydride, an alkali metal borohydride, such as lithium, sodium or potassium borohydride, lithium triethylborohydride (Super-Hydride®), potassium tri(sec-butyl)borohydride (K-Selectride®), potassium tri(siamyl)borohydride (KS-Selectride®), lithium tri(sec-butyl)borohydride(L-Selectride®), lithium tri(siamyl)borohydride (LS-Selectride®), sodium tri(sec-butyl)borohydride (N-Selectride®), an alkali metal aminoborohydride or alkali metal (mono- or di-substituted amino)borohydride, such as lithium aminoborohydride, sodium dimethylaminoborohydride, lithium diethylaminoborohydride, lithium di-n-propyl-aminoborohydride, lithium diisopropylaminoborohydride, lithium 1-azaheptano-borohydride, lithium pyrrolidino-borohydride, lithium morpholino-borohydride, lithium piperidino-borohydride, lithium (N-ethyl-N-phenyl-amino) borohydride, sodium bis(2-methoxyethoxy)aluminium hydride (Vitride®), lithium aluminium hydride, lithium tri (methoxy)aluminium hydride, diisobutylaluminium hydride (Dibal) (especially preferred) or lithium tri(tert-butoxy) aluminium hydride, in a suitable solvent or solvent mixture, especially an ether, such as tetrahydrofuran (especially preferred), a di-lower alkyl ether, such as diethyl ether or dioxane, a halogenated hydrocarbon, such as dichloromethane or chloroform, esters, such as lower alkyl alkanoates, especially ethyl acetate (especially preferred), an alcohol, such as methanol (especially preferred) or ethanol, or mixtures of some or all of the solvents mentioned, at preferred temperatures of from –10° to 80° C., especially from 0° to 60° C., for example from 0° C. to room temperature (for reagents and reaction conditions see also Heterocycles 14, 1437 (1980); Tetrahedron Lett. 33(32), 4533 (1992); U.S. Pat. No. 4,895,943; Synthet. Commun. 21, 1579 (1991); J. Chem. Soc. Perkin I, 1011 (1986); J. Org. Chem. 45, 1 (1980); or Bioorganic & Medicinal Chemistry Letters 4(16), 2055 (1994)).

When hydrogenation is carried out with a suitable complex hydride or with hydrogen in the presence of a suitable catalyst and acyl migration starting from a hydrazone of formula III, the procedure is preferably as follows:

First the hydrogenation is carried out:

As the complex hydride suitable for the hydrogenation there is used especially an alkali metal borohydride, such as an alkali metal cyanoborohydride, especially sodium cyanoborohydride ($NaBH_3CN$), in the presence of an acid, preferably a relatively strong acid, such as a mineral acid, for example sulfuric acid, phosphoric acid, hydrochloric acid, hydrobromic acid or hydrofluoric acid, or especially an organic sulfonic acid, for example an alkanesulfonic acid, such as methanesulfonic acid, or an aromatic sulfonic acid, especially 4-toluenesulfonic acid, the reaction being carried out in a suitable solvent, especially an ether, such as tetrahydrofuran or in a broader sense also dioxane, (see also Tetrahedron Lett. 49, 8605 (1993)), in the presence of water or in the absence thereof, at preferred temperatures of from 0° to 80° C., especially from 10° to 60° C., for example approximately at room temperature.

The hydrogenation with hydrogen in the presence of a suitable catalyst, especially nickel, rhodium, ruthenium, palladium and platinum catalysts, more especially Raney nickel or palladium or platinum catalysts, optionally on carriers, such as active carbon, aluminium oxide or barium sulfate, is preferably carried out at a hydrogen pressure of from 0.1 to 200 bar, preferably from 1 to 100 bar, and at preferred temperatures of from 20° to 120° C., especially from 40° to 100° C., preferably in the presence of one or more organic solvent(s), such as an alkanol, such as methanol, ethanol, isopropanol, sec-butanol or tert-butanol, an ether, such as diethyl ether, tetrahydrofuran or dioxane, an amide, such as N,N-dimethylformamide or N,N-diethylformamide, an aromatic hydrocarbon, such as toluene or xylene, an aliphatic monocarboxylic acid, such as a lower alkanoic acid, for example formic acid, acetic acid, propionic acid, butyric acid, isobutyric acid, iso- and n-valeric acid, or an ester, such as an alkyl ester of aliphatic monocarboxylic acids, for example methyl or ethyl formate, methyl, ethyl, n-butyl or isobutyl acetate, esters of carbonic acid, such as dimethyl or diethyl carbonate, or mixtures of one or more of the solvent(s) mentioned, with special preference being given to acetic acid, methanol, ethanol, isopropanol, sec-butanol, tert-butanol or mixtures of those alcohols with ethyl acetate.

Hydrogenation with complex hydrides is preferred over hydrogenation with hydrogen in the presence of a suitable catalyst.

A borate complex is obtained which is either (preferably) worked up and isolated, for example by partition, for example between an aqueous phase and an organic phase comprising an ester, such as ethyl acetate, as solvent, and (if necessary after drying, for example over sodium sulfate) concentration by evaporation of the phase containing the borate complex, or is used further directly in situ.

It is preferable, because especially few by-products are then formed, for the working-up to be carried out by the addition of a weakly alkaline buffer, for example by the addition of an alkali metal borate, such as sodium tetraborate or potassium tetraborate ($K_2B_4O_7$) in water, resulting in a product in which the radical $R_3$—$(CH_2)_{m-1}$—$C(=O)$— is still attached to the oxygen atom and which is no longer in the form of a borate complex. That intermediate is then preferably worked up and isolated, for example by precipitation and washing of the precipitated product (for example with water) and taking up in an ester, such as ethyl acetate, partition between the organic phase and an aqueous solution, for example brine, and concentration of the organic phase by evaporation (if necessary after drying, for example over sodium sulfate).

The subsequent acyl migration of the radical $R_3$—$(CH_2)_{m-1}$—$C(=O)$— from the oxygen atom in formula III to the hydrazine nitrogen atom in formula II preferably is carried out under basic reaction conditions, especially in the presence of an aqueous base, especially an aqueous alkali metal hydroxide, such as potassium or sodium hydroxide, or preferably in the presence of a strong organic base, especially an aprotic nitrogen base, such as 1,8-diazabicyclo[5.4.0]undec-7-ene(1,5-5) or especially 7-methyl-1,5,7-triazabicyclo[4.4.0]dec-5-ene, in the absence or presence of one or more further solvent(s), such as ethers, preferably a dioxane or di-lower alkoxy-lower alkane, such as 1 2-dimethoxyethane, or a bis(lower alkoxy-lower alkyl) ether, such as diethylene glycol dimethyl ether, at preferred temperatures of from −10° to 100° C., especially from 0° to 90° C., for example from −10° C. to 60° C., especially from 0° to 30° C., and result in a corresponding compound of formula II.

The selective catalytic hydrogenation of the nitrile group in a compound of formula IV is preferably carried out directly in the presence of the hydrazine derivative of formula VI and without isolation of the imino compound of formula V using types of catalyst known per se, especially cobalt, nickel and noble metal catalysts, such as platinum, rhodium, palladium and ruthenium catalysts, which are used in free form or bonded to carriers, such as active carbon, aluminium oxide or barium sulfate, with special preference being given to rhodium on carriers, such as active carbon or aluminium oxide, or especially Raney nickel; in the presence of hydrogen, preferably molecular hydrogen;

an acid, it being possible to use an inorganic or organic acid, especially an inorganic protonic acid, such as a hydrohalic acid, for example HCl, HBr or HF, phosphoric acid or sulfuric acid, or an organic protonic acid, for example a sulfinic acid, such as benzenesulfinic acid, an aliphatic and unsubstituted or substituted aromatic sulfonic acid, such as methanesulfonic acid, benzenesulfonic acid, p-toluenesulfonic acid, naphthalenesulfonic acid or naphthalenedisulfonic acid, an aliphatic monocarboxylic acid having preferably from 1 to 18 carbon atoms, such as formic acid, acetic acid, propionic acid, butyric acid, lauric acid, palmitic acid or stearic acid, a halogenated aliphatic monocarboxylic acid, such as chloroacetic acid, dichloroacetic acid, trichloroacetic acid or trifluoroacetic acid, an aliphatic dicarboxylic acid having preferably from 2 to 12 carbon atoms, such as oxalic acid, malonic acid, succinic acid, adipoic acid or sebacic acid, an unsubstituted or substituted aromatic mono- or di-carboxylic acid, such as benzoic acid, toluic acid, naphthoic acid, phthalic acid or terephthalic acid; preferably a weak acid, such as an aliphatic monocarboxylic acid having from 1 to 4 carbon atoms, such as formic acid, propionic acid, butyric acid or especially acetic acid; the acid and the hydrazine derivative of formula VI advantageously being used in an at least equimolar amount, based on the compound of formula IV, with the hydrazine derivative preferably being used in an equimolar to twice the molar amount and the acid in an equimolar to four times the molar amount, and it being possible, where appropriate, for excess acid to be used directly as solvent;

in the presence or absence of an organic or aqueous organic solvent or solvent mixture, especially in the presence of an alcohol, for example a lower alkanol, such as methanol, ethanol, n-propanol, isopropanol, butanol or pentanol, or an aliphatic or cyclic ether, such as diethyl ether, di-n-propyl ether, diisopropyl ether, tetrahydropyran, tetrahydrofuran or dioxane; or a cyclic or aliphatic amide, such as N-methyl-2-pyrrolidone, N-acetyl-2-pyrrolidone, formamide, an N,N-dialkylamide of an aliphatic monocarboxylic acid having from 1 to 3 carbon atoms in the acid moiety, such as N,N-dimethylformamide, N,N-dimethylacetamide and N,N-diethylacetamide, and/or mixtures of the solvents mentioned with one another or with water, with special preference being given to reaction in a $C_1$–$C_4$alkanol, especially methanol or ethanol, or in mixtures thereof with water;

at preferred temperatures of from 0° to 150° C., especially from 20° to 60° C.;

under normal pressure or under elevated pressure, preferably from normal pressure to a pressure of up to 10 bar, preferably up to 4 bar.

Alternatively it is also possible first to carry out the hydrogenation to give an imino compound of formula V which, without being isolated or after being fully or partially isolated, is then reacted with the hydrazine derivative of formula VI, the reaction conditions preferably corresponding to those last mentioned.

For the reaction with a reactive derivative of a carboxylic acid of formula VII there is used as reactive derivative especially a compound of formula IX

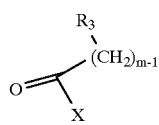

(IX)

wherein $R_3$ and m are as defined for compounds of formula I and wherein X is halogen, especially chlorine, or a radical of an acid bonded via an oxygen atom, especially of a corresponding carboxylic acid, for example an acyloxy radical of the carboxylic acid of formula VIII itself [radical $R_3$—$(CH_2)_{m-1}$—C(=O)—O— (symmetric anhydride)] or especially lower alkanoyloxy, such as acetyloxy, or lower alkoxycarbonyloxy, such as isobutyloxycarbonyloxy; as cyanide salt there is preferably used an alkali metal cyanide, especially potassium or sodium cyanide; the reaction is preferably carried out under phase transfer conditions in the presence of a quaternary ammonium salt, especially tricaprylmethylammonium halide, such as tricaprylmethylammonium chloride (Aliquat), tetraalkylammonium halide, such as tetrabutylammonium chloride, trialkyl-aryl-lower alkylammonium halide, such as benzyltriethyl-ammonium chloride, benzylcinchoninium halide, such as benzylcinchoninium chloride, benzylcinchonidinium halide, such as benzylcinchonidinium chloride, or benzylquininium halide, such as benzylquininium chloride, in a suitable aqueous solvent mixture, such as mixtures of one or more halogenated hydrocarbon(s) with water, especially methylene chloride/water, 1,1-dichloroethane/water or chloroform/water, or mixtures of one or more aliphatic ether(s) with water, such as a dialkyl ether/water, for example diethyl ether/water, or cyclic ethers/water, such as tetrahydrofuran/water or dioxane/water (phase separation especially in the case of a high salt concentration). The reaction takes place at preferred temperatures of from −20° to 50° C., especially from approximately 0° C. to room temperature.

The reaction to form a compound of formula IV, especially IV', starting from a reactive acid derivative of a compound of formula VIII and an aldehyde of formula VII, especially VII', is preferably carried out stereoselectively, so that the molar ratio of the resulting compound of formula IV wherein the asymmetric carbon atom carrying the cyano group is in the (R)-configuration to that wherein the asymmetric carbon atom carrying the cyano group is in the (S)-configuration is greater than approximately 3:1 and is especially from 4:1 to 10:1. Preference is given here to the reaction of a starting compound of formula VIII', as defined above, with an aldehyde of formula VII' that preferably stereoselectively results in a mixture of the conformational isomers of formulae IV'a and IV'b

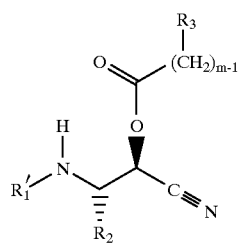

(IV'a)

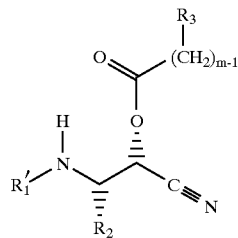

(IV'b)

wherein the molar ratio of the isomers of formulae IV'a:IV'b is greater than 3, and is especially from 4 to 10.

Alternatively it is also possible for the reaction of an aldehyde of formula VII, especially of formula VII', with hydrocyanic acid in the presence of the enzyme (S)-oxynitrilase, which can be obtained from almonds, either in the presence of almonds or almond extracts or the purified (S)-oxynitrilase itself, or preferably in the presence of the enzyme (R)-oxynitrilase from Sorghum bicolor, which can be used in the form of cells, cell extracts or in purified form, in organic solvents, to be carried out stereoselectively, followed by acylation with an acid of formula VIII or a reactive acid derivative thereof, as described above (see Tetrahedron Asymmetry 7(3), 663–666 (1996)).

When further functional groups, for example carboxy, hydroxy, amino or mercapto groups, in the compounds of formulae I to VIII are present in protected form or have to be present in protected form because they are not to participate in the reaction, the protecting groups are those such as are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis and the like. In certain cases the protecting groups can additionally cause reactions to proceed selectively, for example stereoselectively. It is characteristic of protecting groups that they can be removed easily, i.e. without undesired secondary reactions taking place, for example by solvolysis, photolysis, and also enzymatically, for example under physiological conditions; or in a broader sense also by means of reduction, in which case it will be necessary after one of the reductions and/or hydrogenations mentioned hereinabove and hereinbelow to re-introduce functional groups if required for further reactions. The person skilled in the art will know or can readily find out which protecting groups are stable in the reductions and/or hydrogenations mentioned hereinabove and hereinbelow.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie"("Methods of Organic Chemistry"), Houben-Weyl, 4th edition, Volume 15/I, Georg Thieme Verlag, Stuttgart 1974, in H. -D. Jakubke and H. Jescheit, "Aminosäuren, Peptide, Proteine"("Amino acids, peptides, proteins"), Verlag Chemie, Weinheim, Deerfield Beach and Basle 1982, and in Jochen Lehmann, "Chemie der Kohlenhydrate: Monosaccharide und Derivate"("The Chemistry of Carbohydrates: monosaccharides and derivatives"), Georg Thieme Verlag, Stuttgart 1974.

Starting materials of formula VI, of formula VII, of formula VIII and of formula IX are known or can be prepared by procedures known per se. The same applies to the other reagents used in the mentioned reactions.

In the preferred subjects of the invention mentioned below, it is possible, where expedient and advantageous, to replace general definitions by the more specific definitions mentioned hereinabove or hereinbelow.

Preference is given to a process for the preparation of a compound of formula I

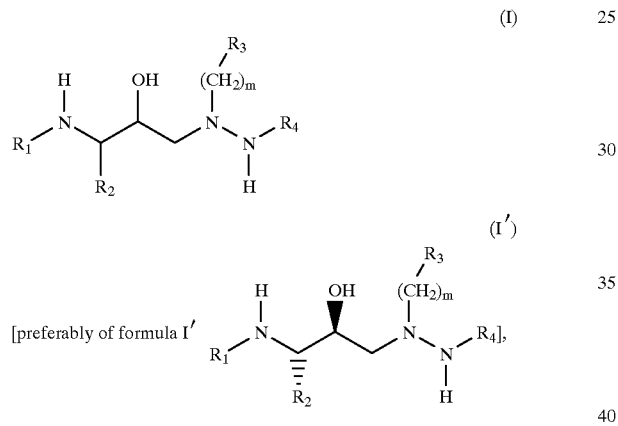

wherein
$R_1$ is hydrogen, 1-[1-adamantyl]-1-methylethoxycarbonyl, isobornyloxycarbonyl, cyclopentyloxycarbonyl, 5,5-dimethyl-3-oxo-cyclohexen-1-yl or especially tert-lower alkoxycarbonyl, such as tert-amyloxycarbonyl and especially tert-butoxycarbonyl;

$R_2$ is lower alkyl, especially methyl, that is unsubstituted or preferably substituted by phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]-pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl; or by $C_3$–$C_8$cycloalkyl, especially cyclohexyl;

and is preferably phenylmethyl, 4-biphenylylmethyl or especially 4-pyridylphenylmethyl, such as 4-(pyridin-2-yl)phenylmethyl, especially phenylmethyl; most especially 4-(pyridin-2-yl)phenylmethyl;

$R_3$ is phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl; or is $C_3$–$C_8$cycloalkyl, especially cyclohexyl;

and is preferably phenyl, 4-biphenylyl or especially 4-pyridylphenyl, such as 4-(pyridin-2-yl)phenyl;

$R_4$, independently of $R_1$, is hydrogen or one of the radicals mentioned for $R_1$; and m is from 1 to 4, preferably 1;

or of a salt thereof where a salt-forming group is present;

wherein the preparation is carried out by reduction of an oxo compound of formula II

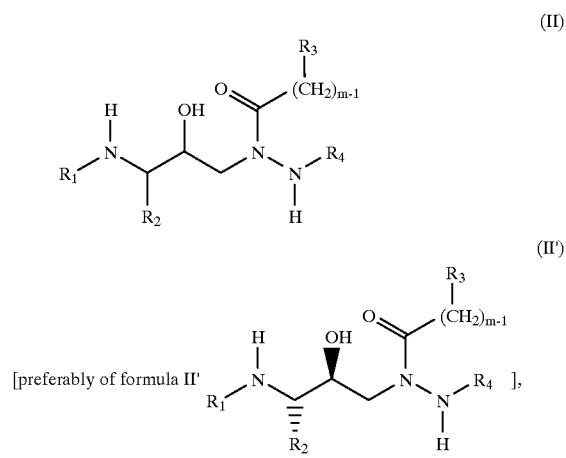

wherein $R_1$, $R_2$, $R_3$, $R_4$ and m are as defined for compounds of formula I, which compound is in turn prepared by hydrogenation with a suitable complex hydride and acyl migration starting from a hydrazone of formula III

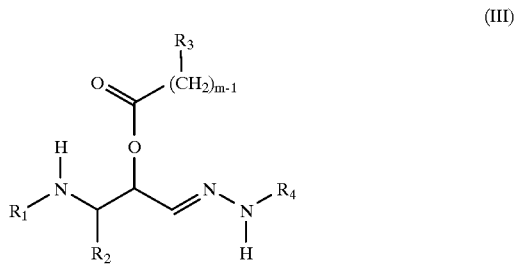

(III')

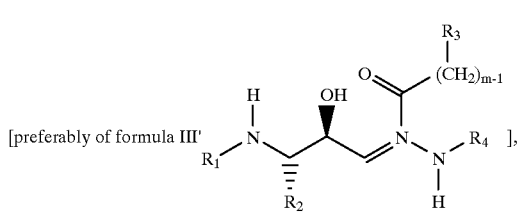

[preferably of formula III']

wherein $R_1$, $R_2$, $R_3$, $R_4$ and m are as defined for compounds of formula I, which is in turn obtained starting from a nitrile of formula IV (IV)

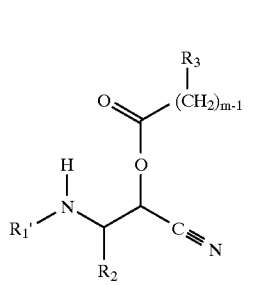

(IV')

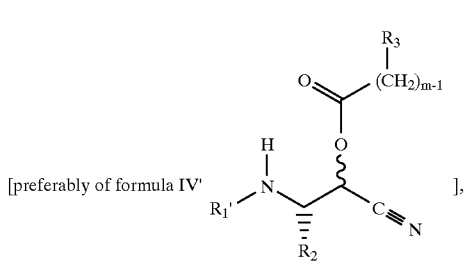

[preferably of formula IV']

wherein $R_1'$ has one of the definitions given for $R_1$ under formula I with the exception of hydrogen and $R_2$, $R_3$ and m are as defined for compounds of formula I, by means of selective catalytic hydrogenation ((preferably) via an imino compound of formula V (V)

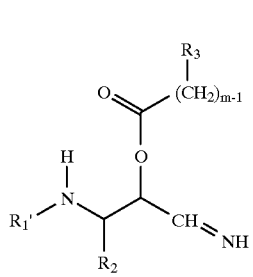

(V')

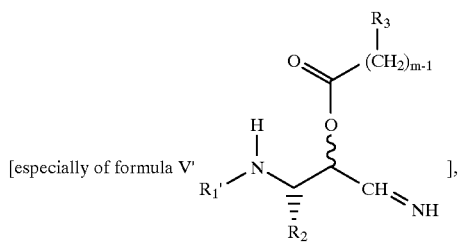

[especially of formula V']

wherein $R_1'$ has one of the definitions mentioned for $R_1$ with the exception of hydrogen and $R_2$, $R_3$ and m are as defined for compounds of formula I), and by reaction with a hydrazine derivative of formula VI (VI)

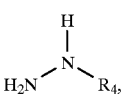

wherein $R_4$ is as defined for a compound of formula I; the hydrazine derivative being added during the selective catalytic hydrogenation, the compound of formula IV being prepared from an aldehyde of formula VII (VII)

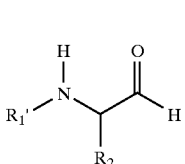

(VII')

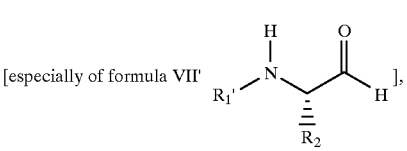

[especially of formula VII']

wherein $R_1'$ has one of the definitions mentioned for $R_1$ under formula I with the exception of hydrogen;

by reaction with a reactive derivative of a carboxylic acid of formula IX (IX)

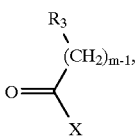

wherein $R_3$ and m are as defined for compounds of formula I and wherein X is halogen, especially chlorine, or a radical of a carboxylic acid of formula VIII itself bonded via an oxygen atom [radical $R_3$—

(CH$_2$)$_{m-1}$—C(=O)—O—(symmetric anhydride)] or especially lower alkanoyloxy, such as acetyloxy, or lower alkoxycarbonyloxy, such as isobutyloxycarbonyloxy;

in the presence of a cyanide salt;

it being possible for the compounds of formulae II to VIII (preferably II' to VIII') to be used in free form or, where salt-forming groups are present, in the form of their salts;

wherein preferably the reduction of an oxo compound of formula II [preferably of formula II'] is carried out using borane/tetrahydrofuran (especially preferred), borane/dimethyl sulfide, tetra(n-butyl)ammonium borohydride, lithium borohydride, sodium borohydride, potassium borohydride, lithium triethylborohydride, potassium tri(sec-butyl) borohydride, potassium tri(siamyl)borohydride, lithium tri(sec-butyl)borohydride, lithium tri(siamyl) borohydride, sodium tri(sec-butyl)borohydride, lithium aminoborohydride, sodium dimethylaminoborohydride, lithium diethylaminoborohydride, lithium di-n-propyl-aminoborohydride, lithium diisopropylaminoborohydride, lithium 1-azaheptano-borohydride, lithium pyrrolidino-borohydride, lithium morpholino-borohydride, lithium piperidino-borohydride, lithium (N-ethyl-N-phenyl-amino)-borohydride, sodium bis(2-methoxyethoxy)aluminium hydride, lithium aluminium hydride, lithium tri(methoxy)aluminium hydride, diisobutylaluminium hydride (especially preferred) or lithium tri(tert-butoxy)aluminium hydride, in an ether, such as tetrahydrofuran (especially preferred), a di-lower alkyl ether, such as diethyl ether or dioxane, or a halogenated hydrocarbon, such as dichloromethane or chloroform, an ester, such as a lower alkyl alkanoate, especially ethyl acetate (especially preferred), an alcohol, such as methanol (especially preferred) or ethanol, or mixtures of some or all of the solvents mentioned, at temperatures of from $-10°$ to $80°$ C., especially from $0°$ to $60°$ C., for example from $0°$ C. room temperature;

for the hydrogenation with a suitable complex hydride and acyl migration starting from a hydrazone of formula III [preferably of formula III'] there is used as the complex hydride an alkali metal cyanoborohydride, especially sodium cyanoborohydride (NaBH$_3$CN), in the presence of sulfuric acid, phosphoric acid, hydrochloric acid, hydrobromic acid or hydrofluoric acid, or especially in the presence of an alkanesulfonic acid, such as methanesulfonic acid, or an aromatic sulfonic acid, especially 4-toluenesulfonic acid, the reaction being carried out in an ether, such as tetrahydrofuran or in a broader sense also dioxane, in the presence of water or in the absence thereof, at temperatures of from $0°$ to $80°$ C., especially from $10°$ to $60°$ C., for example approximately at room temperature; the resulting borate complex is used further after being worked up, for example by partition, for example between an aqueous phase and an organic phase containing an ester, such as ethyl acetate, as solvent and (if necessary after drying, for example over sodium sulfate) concentration by evaporation of the phase containing the borate complex, or is used further directly in situ; or preferably the borate complex is hydrolysed by the addition of a weakly alkaline buffer, for example by the addition of an alkali metal borate, such as sodium tetraborate or potassium tetraborate, and the resulting compound, wherein the radical R$_3$—(CH$_2$)$_{m-1}$—C(=O)— is still attached to the oxygen atom, is preferably worked up and isolated, especially by precipitation and washing of the precipitated product (for example with water) and taking up in an ester, such as ethyl acetate, partition between the organic phase and an aqueous solution, for example brine, and concentration of the organic phase by evaporation (if necessary after drying, for example over sodium sulfate); and the acyl migration of the radical R$_3$—(CH$_2$)$_{m-1}$—C(=O)— from the oxygen atom in formula III [preferably formula III'] to the hydrazine nitrogen atom in formula II [preferably formula II'] is carried out in the presence of an aqueous base, especially an aqueous alkali metal hydroxide, such as potassium or sodium hydroxide, or preferably in the presence of a strong organic base, especially an aprotic nitrogen base, such as 1,8-diazabicyclo[5.4.0]undec-7-ene(1,5-5) or especially 7-methyl-1,5,7-triazabicyclo[4.4.0]dec-5-ene, in the absence or presence of further solvents, such as an ether, preferably dioxane or a di-lower alkoxy-lower alkane, such as 1,2-dimethoxyethane, or a bis(lower alkoxy-lower alkyl) ether, such as diethylene glycol dimethyl ether, at temperatures of from $-10°$ to $100°$ C., especially from $0°$ to $90°$ C., for example from $-10°$ to $60°$ C., especially from $0°$ to $30°$ C.;

the selective catalytic hydrogenation starting from a nitrile of formula IV [especially of formula IV'] and reaction with a hydrazine derivative of formula VI, the hydrazine derivative being added during the selective catalytic hydrogenation, are carried out using cobalt or especially nickel catalysts, which are used in free form or bonded to active carbon, aluminium oxide or barium sulfate, with special preference being given to Raney nickel, in the presence of molecular hydrogen, and an aliphatic monocarboxylic acid having preferably from 1 to 18 carbon atoms, such as formic acid, acetic acid, propionic acid, butyric acid, lauric acid, palmitic acid or stearic acid, preferably an aliphatic monocarboxylic acid having from 1 to 4 carbon atoms, such as formic acid, propionic acid, butyric acid or especially acetic acid; the acid and the hydrazine derivative of formula VI advantageously being used in at least equimolar amounts, based on the compound of formula IV [especially of formula IV'], with the hydrazine derivative being used preferably in an equimolar to twice the molar amount and the acid preferably in an equimolar to four times the molar amount, in the presence or absence of an alcohol, for example a lower alkanol, such as methanol, ethanol, n-propanol, isopropanol, butanol or pentanol, or an aliphatic or cyclic ether, such as diethyl ether, di-n-propyl ether, diisopropyl ether, tetrahydropyran, tetrahydrofuran or dioxane; or a cyclic or aliphatic amide, such as N-methyl-2-pyrrolidone, N-acetyl-2-pyrrolidone, formamide, an N,N-dialkylamide of an aliphatic monocarboxylic acid having from 1 to 3 carbon atoms in the acid moiety, such as N,N-dimethylformamide, N,N-dimethylacetamide and N,N-diethylacetamide, and/or mixtures of the solvents mentioned with one another or with water, with special preference being given to reaction in a $C_1$–$C_4$alkanol, especially methanol or ethanol, or in mixtures thereof with water; at temperatures of from 0° to 150° C., especially from 20° to 60° C.; at pressures from normal pressure to a pressure of up to 10 bar, preferably up to 4 bar; and for the reaction of an aldehyde of formula VII [especially of formula VII'] with a reactive derivative of a carboxylic acid of formula IX in the presence of a cyanide salt there is preferably used an alkali metal cyanide, especially potassium or sodium cyanide; and the reaction is carried out especially under phase transfer conditions in the presence of a quaternary ammonium salt, especially a tricaprylmethylammonium halide, such as tricaprylmethylammonium chloride (Aliquat), tetraalkylammonium halide, such as tetrabutylammonium chloride, trialkyl-aryl-lower alkylammonium halide, such as triethylbenzylammonium chloride, benzylcinchoninium halide, such as benzylcinchoninium chloride, benzylcinchonidinium halide, such as benzylcinchonidinium chloride, or benzylquininium halide, such as benzylquininium chloride, in mixtures of a halogenated hydrocarbon with water, especially methylene chloride/water, 1,1-dichloroethane/water or chloroform/water, or mixtures of an aliphatic ether with water, such as a dialkyl ether/water, for example diethyl ether/water, or cyclic ether/water mixtures, such as tetrahydrofuran/water or dioxane/water (phase separation especially in the case of a high salt concentration), at temperatures of from –20° to 50° C., especially from approximately 0° C. to room temperature; the reaction preferably being carried out stereoselectively, as indicated above.

Special preference is given to a process for the preparation of a compound of formula I wherein $R_1$ is tert-butoxycarbonyl, $R_2$ is phenylmethyl, $R_3$ is 4-biphenylyl, $R_4$ is tert-butoxycarbonyl and m is 1 that is carried out starting from appropriately substituted starting materials, as defined hereinabove or hereinbelow.

Special preference is given also to a process for the preparation of a compound of formula I wherein $R_1$ is tert-butoxycarbonyl, $R_2$ is phenylmethyl, $R_3$ is phenyl, $R_4$ is tert-butoxycarbonyl and m is 1 that is carried out starting from appropriately substituted starting materials, as defined hereinabove or hereinbelow.

Special preference is given also to a process for the preparation of a compound of formula I wherein $R_1$ is tert-butoxycarbonyl, $R_2$ is phenylmethyl, $R_3$ is 4-(pyridin-2-yl)phenyl, $R_4$ is tert-butoxycarbonyl and m is 1, or a salt thereof, that is carried out starting from appropriately substituted starting materials, as defined hereinabove or hereinbelow.

Special preference is given also to a process for the preparation of a compound of formula I wherein $R_1$ is hydrogen, $R_2$ is phenylmethyl, $R_3$ is 4-(pyridin-2-yl)phenyl, $R_4$ is hydrogen and m is 1, or a salt thereof, that is carried out starting from appropriately substituted starting materials, as defined hereinabove or hereinbelow.

Preference is given also to processes for the preparation of intermediates that correspond to one or more of the sub-reactions mentioned hereinabove and hereinbelow, especially (i) a process for the preparation of a compound of formula IV, especially IV', which process comprises the reaction of an aldehyde of formula VII, especially VII', with a reactive derivative of a carboxylic acid of formula VIII in the presence of a cyanide salt, preferably the stereo-selective reaction that results in the molar ratios of conformational isomers of formula IV mentioned hereinabove and hereinbelow as being preferred, (ii) a process for the preparation of a hydrazone of formula III, especially III', which process comprises the reaction of the nitrile of formula IV, especially IV', by selective catalytic hydrogenation (optionally with isolation of an imino compound of formula V, especially V') and reaction with a hydrazine derivative of formula VI to form the corresponding hydrazone of formula III, especially II'; or (iii) a process for the preparation of an oxo compound of formula II, especially IV', which process comprises the hydrogenation with a suitable complex hydride or hydrogen in the presence of a suitable catalyst and acyl migration for the reaction of a hydrazone of formula III, especially III', to form an oxo compound of formula II, especially II';

or combinations of (i) and (ii), (ii) and (iii) or (i), (ii) and (iii); special preference being given to the conditions mentioned hereinabove and hereinbelow as being preferred; and it being possible for the starting materials and the respective products to be in the form of salts where salt-forming groups are present and for further suitable protecting groups for functional groups to be present in the relevant starting materials and products.

Of the intermediates as such, the invention relates especially to the following compounds:

Preference is given to a nitrile of formula IV

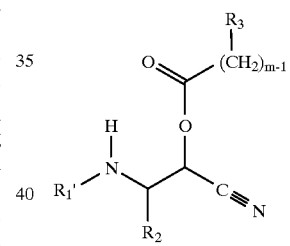

(IV)

[preferably of formula IV'

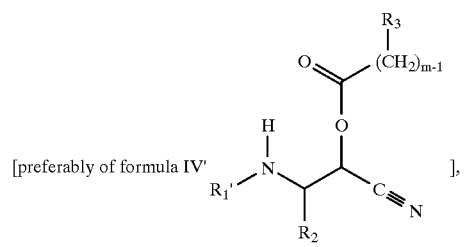

(IV')

], wherein
$R_1'$ is an amino-protecting group,
$R_2$ is lower alkyl, especially methyl, that is unsubstituted or preferably substituted by aryl or by heterocyclyl, and is especially benzyl,
$R_3$ is phenyl substituted with phenyl or preferably heterocyclyl, especially 4-(2-methyl-2H-tetrazol-5-yl)-phenyl, 4-(thiazol-2-yl)-phenyl or more especially 4-(2-pyridyl)phenyl, and
m is 1 or 2, preferably 1;
and wherein further suitable protecting groups for functional groups may be present;
or a salt thereof where a salt-forming group is present.

Of those compounds, special preference is given to compounds of formula IV' wherein R$_1$' is tert-lower alkoxycarbonyl, especially tert-butoxycarbonyl;

R$_2$ is lower alkyl, especially methyl, that is unsubstituted or preferably substituted by phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]-pyranyl, with heterocyclyl being unsubstituted or substituted by hydroxy, halogen, oxo, lower alkylimino, amino, lower alkylamino, di-lower alkylamino, lower alkoxy, halo-lower alkyl, C$_3$–C$_8$cycloalkyl, phenyl, phenyl-lower alkyl, carboxy, sulfo or by lower alkyl; or by C$_3$–C$_8$cycloalkyl, especially cyclohexyl;

and is preferably phenylmethyl, 4-biphenylylmethyl or also 4-pyridylphenylmethyl, such as 4-(pyridin-2-yl)phenylmethyl, especially phenylmethyl;

R$_3$ is phenyl that is substituted by one or more (preferably up to 3, especially 2 or more especially one) phenyl or (preferably) heterocyclyl substituent(s), heterocyclyl being selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, C$_3$–C$_8$cycloalkyl, phenyl, phenyl-lower alkyl, carboxy, sulfo or by lower alkyl;

and is preferably 4-biphenylyl or especially 4-(2-methyl-2H-tetrazol-5-yl)-phenyl, 4-(thiazol-2-yl)-phenyl or more especially pyridylphenyl, such as 4-(pyridin-2-yl)phenyl; and m is 1;

or salts thereof where salt-forming groups are present.

Preference is given also to an imino compound of formula V

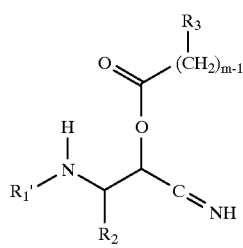

(V)

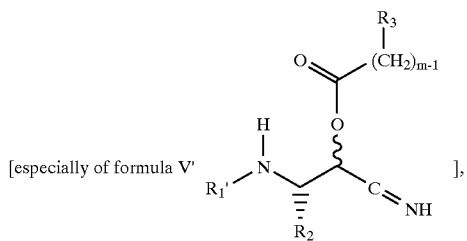

wherein

R$_1$' is an amino-protecting group;

R$_2$ is substituted alkyl, especially lower alkyl, more especially methyl, that is unsubstituted or preferably substituted by aryl or by heterocyclyl, and is especially benzyl, R$_3$ is hydrogen, aryl, heterocyclyl, unsubstituted or substituted alkyl or unsubstituted or substituted cycloalkyl, and is especially 4-(2-methyl-2H-tetrazol-5-yl)-phenyl, 4-(thiazol-2-yl)- phenyl or more especially pyridylphenyl, such as 4-(pyridin-2-yl)phenyl, and m is a number from 1 to 7;

and wherein further suitable protecting groups for functional groups may be present;

or a salt thereof where a salt-forming group is present.

Special preference is given to compounds of formula V' wherein

R$_1$' is tert-lower alkoxycarbonyl, especially tert-butoxycarbonyl;

R$_2$ is lower alkyl, especially methyl, that is unsubstituted or preferably substituted by phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]-pyranyl, with heterocyclyl being unsubstituted or substituted by hydroxy, halogen, oxo, lower alkylimino, amino, lower alkylamino, di-lower alkylamino, lower alkoxy, halo-lower alkyl, C$_3$–C$_8$cycloalkyl, phenyl, phenyl-lower alkyl, carboxy, sulfo or by lower alkyl; or by C$_3$–C$_8$cycloalkyl, especially cyclohexyl;

and is preferably phenylmethyl, 4-biphenylylmethyl or 4-pyridylphenylmethyl, such as 4-(pyridin-2-yl)phenyl, especially phenylmethyl;

R$_3$ is phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl; or is $C_3$–$C_8$cycloalkyl, especially cyclohexyl;

and is preferably phenyl, 4-biphenylyl or especially 4-(2-methyl-2H-tetrazol-5-yl)-phenyl, 4-(thiazol-2-yl)-phenyl or more especially 4-pyridylphenyl, such as 4-(pyridin-2-yl)phenyl; and m is 1;

or salts thereof where salt-forming groups are present.

Preference is given also to a hydrazone of formula III

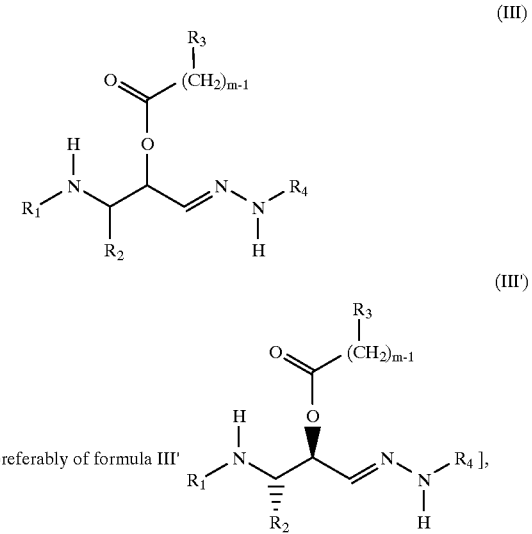

[preferably of formula III']

wherein

R$_1$ is hydrogen or a suitable amino-protecting group;

R$_2$ is unsubstituted or substituted alkyl, especially lower alkyl, more especially methyl, that is unsubstituted or preferably substituted by aryl or by heterocyclyl, and is especially benzyl, R$_3$ is hydrogen, aryl, heterocyclyl, substituted alkyl or unsubstituted or substituted cycloalkyl, and is preferably phenyl, 4-biphenylyl or especially 4-(2-methyl-2H-tetrazol-5-yl)-phenyl, 4-(thiazol-2-yl)-phenyl or more especially 4-pyridylphenyl, such as 4-(pyridin-2-yl)phenyl, R$_4$, independently of R$_1$, is hydrogen or a suitable amino-protecting group and m is a number from 1 to 7;

and wherein further suitable protecting groups for functional groups may be present;

or a salt thereof where a salt-forming group is present.

Of those, special preference is given to compounds of formula III' wherein

R$_1$ is hydrogen or tert-lower alkoxycarbonyl, especially tert-butoxycarbonyl;

R$_2$ is lower alkyl, especially methyl, that is unsubstituted or preferably substituted by phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]-pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl; or by $C_3$–$C_8$cycloalkyl, especially cyclohexyl;

and is preferably phenylmethyl, 4-biphenylylmethyl or also 4-pyridylphenylmethyl, such as 4-(pyridin-2-yl)phenylmethyl, especially phenylmethyl;

R$_3$ is phenyl that is unsubstituted or substituted by one or more (preferably up to 3, especially 2 or more especially one) substituent(s) selected from halogen, such as fluorine or chlorine, nitro, lower alkoxy, such as methoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3$–$C_8$cycloalkyl, phenyl, phenyl-lower alkyl, carboxy, sulfo or by lower alkyl; or is $C_3$–$C_8$cycloalkyl, especially cyclohexyl;

and is preferably phenyl, 4-biphenylyl or especially 4-(2-methyl-2H-tetrazol-5-yl)-phenyl, 4-(thiazol-2-yl)-phenyl or more especially 4-pyridylphenyl, such as 4-(pyridin-2-yl)phenyl;

R$_4$ is hydrogen or tert-lower alkoxycarbonyl, especially tert-butoxycarbonyl; and m is 1;

or salts thereof where salt-forming groups are present.

Preference is given also to processes for the preparation of the intermediates last described as being subjects of the invention that correspond to one or more of the sub-reactions mentioned hereinabove and hereinbelow, especially (i) a process for the preparation of a respective compound of formula IV, especially IV', which process comprises the reaction of a corresponding aldehyde of formula VII, especially VII', with a reactive derivative of a carboxylic acid of formula VIII in the presence of a cyanide salt, preferably the stereoselective reaction that results in the molar ratios of conformational isomers of formula IV mentioned hereinabove and hereinbelow as being preferred, or (ii) a process for the preparation of a respective hydrazone of formula II, especially III', which process comprises the reaction of the corresponding nitrile of formula IV, especially IV', by selective catalytic hydrogenation (optionally with isolation of an imino compound of formula V, especially V') and reaction with a hydrazine derivative of formula VI to form the corresponding hydrazone of formula III, especially III';

or combinations of (i) and (ii); special preference being given to the conditions mentioned hereinabove and hereinbelow as being preferred; and it being possible for the starting materials and the respective products to be in the form of salts where salt-forming groups are present and for further suitable protecting groups for functional groups to be present in the relevant starting materials and products.

Special preference is given to the novel sub-reactions, reactions, reaction conditions, compounds of formula I and intermediates in the Examples given hereinbelow.

The following Examples serve to illustrate the invention but do not limit the scope thereof in any way.

HPLC system used: gradient: 20%→100% a) in b) over 20 min. eluant a): acetonitrile+0.05% TFA; eluant b): water +0.05% TFA. Column (250×4.6 mm) filled with reversed phase material C18-Nucleosil (5 μm average particle size, silica gel covalently derivatised with octadecylsilanes, Macherey & Nagel, Düren, FRG). Detection by UV absorption at 254 nm. The retention times ($t_{Ret}$) are given in minutes. Flow rate 1 ml/min.

Abbreviations used

| | |
|---|---|
| Anal. | elemental analysis |
| atm | atmospheres (pressure unit; 1 atm corresponds to 0.1013 MPa) |
| basic alox | basic aluminium oxide |
| Boc | tert-butoxycarbonyl |
| brine | saturated sodium chloride solution |
| calc. | calculated |
| dimethoxyethane | 1,2-dimethoxyethane |
| DMSO | dimethyl sulfoxide |
| FAB-MS | fast atom bombardment mass spectroscopy |
| h | hour(s) |
| HPLC | high performance liquid chromatography |
| min | minute(s) |
| m.p. | melting point |
| $^1$H-NMR | proton-magnetic nuclear resonance |
| $R_f$ | ratio migration distance/mobile phase front in TLC |
| sat. | saturated |
| THF | tetrahydrofuran |
| TLC | thin-layer chromatography |
| TPTU | O-(1,2-dihydro-2-oxo-1-pyridyl)-N,N,N',N'-tetramethyluronium tetrafluoroborate |

EXAMPLE 1

1-Phenyl-5(S)-2,5-di[(tert-butoxycarbonyl)amino]-4(S)-hydroxy-6-phenyl-2-azahexane 10 ml (10 mmol) of borane-THF complex (1M in THF; Fluka, Buchs, Switzerland) are added at 0° C. to a solution of 1.0 g (2 mmol) of 1-phenyl-1-oxo-5(S)-2,5-[di(tertbutoxycarbonyl)amino]-4(S)-hydroxy-6-phenyl-2-azahexane in 0.5 ml of THF (filtered through basic alox). After 1.5 h at that temperature, the cooling bath is removed and the reaction mixture is stirred at 15° C. for 2.75 h and then at room temperature for 2.75 h. For working up, the reaction mixture is poured into ice-cold 1N sodium hydroxide solution and extracted with methylene chloride. The organic phases are dried over sodium sulfate and concentrated by evaporation. The crude product is purified by chromatography on silica gel (eluant 24:1 methylene chloride:THF) and yields the title compound in the form of a colorless amorphous solid which is digested with diisopropyl ether. M.p. 182–183° C. $^1$H-NMR (CD$_3$OD, 55° C.) δ7.38–7.1 (m, 10H); 4.85 (s, 2H); 4.8–4.65 (m, 2H); 2.95–2.63 (m, 4H); 1.33 (s, 9H); 1.30 (s, 9H). FAB MS (M+H)$^+$=486. Anal. (C$_{27}$H$_{39}$N$_3$O$_5$) C: calc. 66.78; found 66.54; H: calc. 8.09; found 7.86; N: calc. 8.65; found 8.57. TLC: R$_f$(20:1 methylene chloride:THF) 0.65. HPLC: retention time 17.3 min.

The synthesis of the starting material is carried out via the following steps:

Step 1.1

1-(R)-Cyano-2-(S)-(N-tert-butoxycarbonylamino)-3-phenylpropyl benzoate (1a) and 1-(S)-cyano-2(S)-(N-tert-butoxycarbonylamino)-3-phenylpropyl benzoate (1b)

A solution of 4.0 g (60 mmol) of potassium cyanide in 10 ml of water and 10 ml of methylene chloride is cooled to 0° C., and 0.5 g (2.2 mmol) of benzyltriethylammonium chloride (Fluka, Buchs, Switzerland) is added. A solution of 12.42 g (50 mmol) of Boc-(L)-phenylalaninal (preparation: J. Org. Chem. 51, 3921 (1986)) in 15 ml of methylene chloride and a solution of 13.59 g (60 mmol) of benzoic acid anhydride (Fluka, Buchs, Switzerland) in 15 ml of methylene chloride are simultaneously added dropwise thereto at a temperature of 0–5° C. 20 min after the addition is complete, the cooling bath is removed and the reaction mixture is stirred at room temperature for 4 h. The mixture is diluted with 100 ml of methylene chloride and 100 ml of water and the phases are separated. The organic phase is washed three times using 50 ml of water each time, dried over sodium sulfate and concentrated by evaporation. The crude product is purified by chromatography on silica gel (eluant 0.5%→2% methanol in methylene chloride) and yields the title compound as a (5:1) mixture of the two diastereoisomers 1a (5 parts, 1(R)-form) and 1b (1 part, 1(S)-form) in the form of an amorphous solid: $^1$H-NMR (CDCl$_3$) δ=8.05–7.92 (m, 2H), 7.75–7.62 (m, 1H); 7.59–7.45 (m, 2H); 7.29–7.15 (m, 5H); 5.65 (d, J=4.8Hz, 1H, diastereoisomer 1a); 5.55 (d, J=3.3 Hz, 1H, diastereoisomer 1b); 4.80 (d, J=9 Hz, 1H); 4.50 (m, 1H), 3.20 (dd,J=14.4, 8.2 Hz, 1H); 3.00 (dd, J=14.4, 8.2 Hz, 1H); 1.40 (s, 9H).

FAB MS (M+H)+=381. TLC: R$_f$(20:1 methylene chloride:THF) 0.78. HPLC: retention time 16.8 min (both diastereoisomers).

Step 1.2

4-(S)-1,4-Di[(tert-butoxycarbonyl)amino]-3(R)-(benzoyloxy)-5-phenyl-1-azapent-1-ene 1.67 g (27.8 mmol) of acetic acid and 3.67 g (27.8 mmol) of tert-butyl carbazate (Fluka, Buchs, Switzerland) are added to a solution of 10.5 g (27.8 mmol) of a (5:1) mixture of the cyanohydrin esters 1a and 1b in 210 ml of methanol and hydrogenation is carried out in the presence of 5.3 g of ethanol-moistened Raney nickel for 11.5 h at room temperature and 1 atm hydrogen pressure. The resulting suspension is diluted with 500 ml of methanol, heated slightly and filtered over Hyflo (filter aid based on kieselguhr, Hyflo Super Cel®; Fluka, Buchs, Switzerland). The filtrate is concentrated by evaporation and purified by column chromatography on silica gel (eluant 2:1 ethyl acetate:hexane). Crystallisation of the product fractions from ethyl acetate/hexane yields the diastereoisomerically pure title compound. Further chromatography of the mother liquor and crystallisation yield a further quantum of the title compound. M.p. 188–191° C. $^1$H-NMR (MeOD) δ8.13 (d, J=7.8 Hz, 2H); 7.70–7.57 (m, 1H); 7.55–7.42 (m, 2H); 7.32–7.1 (m, 6H); 5.50 (t, J=5 Hz, 1H); 4.30 (m, 1H); 2.98 (dd, J=14.4, 5.6 Hz, 1H); 2.85 (dd, J=14.4, 5.6 Hz, 1H); 1.49 (s, 9H); 1.30 (s, 9H).

FAB MS (M+H)$^+$=498. Anal. (C$_{27}$H$_{35}$N$_3$O$_6$) C: calc. 65.17; found 64.87; H: calc. 7.09; found 7.06; N: calc. 8.44; found 8.57. TLC: R$_f$(20:1 methylene chloride:THF) 0.78. HPLC: retention time 16.9 min.

Step 1.3

1-Phenyl-1-oxo-5(S)-2,5-di[(tert-butoxycarbonyl)amino]-4(S)-hydroxy-6-phenyl-2-azahexane 296 mg (4 mmol) of sodium cyanoborohydride (Fluka, Buchs, Switzerland) are added to a solution of 1.99 g (4 mmol) of 4-(S)-1,4-di[(tert-butoxycarbonyl)amino]-3(R)-(benzoyloxy)-5-phenyl-1-azapent-1-ene in 25 ml of THF (filtered over basic alox). A solution of 760 mg (4 mmol) of 4-toluenesulfonic acid monohydrate (Fluka, Buchs, Switzerland) in 8 ml of THF is added dropwise to the reaction mixture with stirring at room temperature (dropwise addition time: 20 min). After 2.5 h, a further 147 mg of sodium cyanoborohydride and 380 mg of 4-toluenesulfonic acid monohydrate dissolved in 4 ml of THF are added. After a further 2.5 h, the reaction mixture is diluted with 100 ml of ethyl acetate and washed with 100 ml each of sat. sodium chloride solution, 10% bicarbonate solution and sat. sodium chloride solution. The organic phases are dried over sodium sulfate and concentrated by evaporation and yield the corresponding borate complex in the form of a yellow oil. The oil is dissolved in 20 ml of dimethoxyethane, diluted at 0° C. with 20 ml of 1N sodium hydroxide solution and stirred at room temperature for 16 h. The mixture is then neutralised with 18 ml of 1N hydrochloric acid and extracted three times using 50 ml of methylene chloride each time, and the organic extracts are dried over sodium sulfate and concentrated by evaporation. The crude product is purified by chromatography on silica gel (eluant 24:1 methylene chloride:THF) and yields the title compound in the form of an amorphous solid. M.p. 136–137° C. $^1$H-NMR (DMSO-$d_6$, 100° C.) δ8.85 (br, 1H), 7.45 (m, 2H); 7.25–7.19 (m, 3H); 7.18–7.1 (m, 5H); 5.95 (br, 1H); 4.50 (br, 1H), 3.90–3.80 (m, 2H); 3.70–3.30 (m, br, 2H); 2.91 (dd, J=14, 7 Hz, 1H); 2.70 (dd, J=14, 7 Hz, 1H); 1.25 (s, 9H); 1.20 (s, 9H). FAB MS (M+H)$^+$=500. Anal. ($C_{27}H_{37}N_3O_6$) C: calc. 64.94; found 64.64; H calc. 7.46; found 7.33; N: calc. 8.41; found 8.35. TLC: $R_f$(20:1 methylene chloride:THF) 0.42. HPLC: retention time 16.0 min.

EXAMPLE 2

1-(4-Biphenylyl)-5(S)-2,5-di[(tert-butoxycarbonyl) amino]-4(S)-hydroxy-6-phenyl-2-azahexane 10 ml (10 mmol) of borane-THF complex (1M in THF) are added at 0° C. to a solution of 1.02 g (1.77 mmol) of 1-(4-biphenylyl)-1-oxo-5-(S)-2,5-di[(tert-butoxycarbonyl) amino]-4(S)-hydroxy-6-phenyl-2-azahexane in 10 ml of THF (filtered through basic alox). After 1.5 h at that temperature, the cooling bath is removed and the reaction mixture is stirred at room temperature for 2.5 h. The reaction mixture is then poured into 20 ml of 1N sodium hydroxide solution. After the vigorous evolution of gas has subsided, the mixture is diluted with water and extracted with 500 ml of methylene chloride. The organic phases are dried over sodium sulfate and concentrated. The crude product is purified by chromatography on silica gel (eluant 49:1 THF:methylene chloride) and after digestion in diisopropyl ether yields the title compound. M.p. 185–186° C. $^1$H-NMR (DMSO-$d_6$, 150° C.) δ7.6 (m, 2H); 7.53 (m, 2H); 7.42 (m, 4H); 7.32 (m, 1H); 7.23–7.12 (m, 5H); 5.55 (d, br, J=10 Hz, 1H); 4.15 (d, J=4 Hz, 1H); 3.95 (s, 2H); 3.84 (m, 1H); 3.68 (m, 1H); 2.9–2.75 (m, 4H), 1.33 (s, 9H); 1.31 (s, 9H). FAB MS (M+H)$^+$=562. Anal. ($C_{33}H_{43}N_3O_5$) C: calc. 70.56; found 70.16; H: calc. 7.72; found 7.80; N: calc. 7.48; found 7.24. TLC: $R_f$(19:1 methylene chloride:THF) 0.66. HPLC: retention time 19.0 min.

Alternative variant to Example 2

Under a $N_2$ atmosphere, 2.1 ml (2.1 mmol) of a 1.00M solution of diisobutylaluminium hydride in methylene chloride are slowly added dropwise to an ice-cooled solution of 200 mg (0.347 mmol) of 1-(4-biphenylyl)-1-oxo-5(S)-2,5-di[(tert-butoxycarbonyl)amino]-4(S)-hydroxy-6-phenyl-2-azahexane in 5 ml of THF (foams). After 2 h, 7 ml of ethyl acetate are added and after a further 30 min 70 ml of methanol are added. The reaction mixture is heated to room temperature and stirred for 2 h; 0.5 ml of water and 5 g of sodium sulfate are added and the mixture is stirred for a further 1 h to complete the reaction. The salts are filtered off and the filtrate is concentrated by evaporation. Chromatography on silica gel (eluant 2:1 hexane/ethyl acetate) yields 1-(4-biphenylyl)-5(S)-2,5-[di(tert-butyloxycarbonyl)-amino]-4(S)-hydroxy-6-phenyl-2-azahexane, as characterised above.

The synthesis of the starting material is carried out via the following steps:

Step 2.1

1-(R)-Cyano-2(S)-(N-tert-butoxycarbonylamino)-3-phenylpropyl 4-[phenyl]-benzoate (2a) and 1-(S)-cyano-2(S)-(N-tert-butoxycarbonylamino)-3-phenylpropyl 4-[phenyl]-benzoate(2b):

A solution of 8.34 g (128 mmol) of potassium cyanide is added dropwise at 0° C. to a solution of 12.46 g (50 mmol) of Boc-(L)-phenylalaninal, 13.00 g (60 mmol) of 4-biphenylylcarboxylic acid chloride (Fluka, Buchs, Switzerland) and 924 mg (2.2 mmol) of N-benzylcinchoninium chloride (Fluka, Buchs, Switzerland) in 200 ml of THF (filtered through basic alox) (dropwise addition time: 20 min). After that time the cooling bath is removed and the reaction mixture is stirred at room temperature for 4 h. The mixture is diluted with 200 ml each of ethyl acetate and water; the phases are separated and the organic phase is washed with 0.1N hydrochloric acid and 10% bicarbonate solution. The organic extracts are dried over sodium sulfate and concentrated by evaporation. The title compound is obtained as a (4.2:1) mixture of the two diastereoisomers 2a (4.2 parts; 1(R)-form) and 2b (1 part; 1(S)-form) in the form of an amorphous solid. The analytical data are derived from a sample of the pure diastereoisomer 2a crystallised from diisopropyl ether. M.p. 118–120° C. $^1$H-NMR (CDCl$_3$) δ8.10–8.00 (m, 2H), 7.75–7.6 (m, 4H); 7.55–7.25 (m, 8H); 5.65 (d, J=4.8 Hz, 1H); 4.80 (d, J=9 Hz, 1H); 4.50 (m, 1H), 3.20 (dd, J=14.4, 8.2 Hz, 1H), 3.00 (dd, J=14.4, 8.2 Hz, 1H); 1.40 (s, 9H, ). FAB MS (M+H)$^+$=457. Anal. ($C_{28}H_{28}N_2O_4$) C: calc. 73.66; found 73.52; H: calc. 6.18; found 6.06; N: calc. 6.14; found 6.14. TLC: $R_f$(4:1 hexane:ethyl acetate) 0.39. HPLC: retention time 19.0 min.

Step 2.2

4-(S)-1,4-Di[(tert-butoxycarbonyl)amino]-3(R)-[4-biphenylyl]-carbonyloxy-5-phenyl-1-azapent-1-ene 2.4 ml (42 mmol) of acetic acid and 5.7 g (43 mmol) of tert-butyl carbazate are added to a solution of 19.75 g (40 mmol) of a (4.2:1) mixture of 1-(R)-cyano-N-2-(S)-(tert-butoxycarbonyl)-3-phenylpropyl 4-[phenyl]-benzoate (2a) and 1-(S)-cyano-N-2-(S)-(tert-butoxycarbonyl)-3-phenylpropyl 4-[phenyl]-benzoate (2b) in 400 ml of methanol and hydrogenation is carried out in the presence of 10 g of ethanol-moistened Raney nickel for 8 h at room temperature and 1 atm hydrogen pressure. The reaction mixture is diluted with methylene chloride and filtered over Celite® (filter aid based on kieselguhr; Fluka, Buchs, Switzerland). The filtrate is concentrated by evaporation, again dissolved in methylene chloride and washed with 500 ml each of water and 10% sodium hydrogen carbonate solution, dried over sodium sulfate and again concentrated to dryness by evaporation. The crude product is crystallised from acetonitrile and yields the title compound in the form of the diastereoisomerically pure hydrazone. M.p. 178–180° C. $^1$H-NMR (CDCl$_3$) δ8.12 (d, J=7.8 Hz, 2H); 7.82 (s, br, 1H), 7.70–7.57 (m, 4H); 7.55–7.35 (m, 3H); 7.32–7.1 (m, 5H) 5.62 (t, br, J=5 Hz, 1H); 4.94 (d, br, J=8 Hz, 1H); 4.38 (m, br, 1H); 2.95 (m, 2H); 1.47 (s, 9H); 1.32 (s, 9H). FAB MS (M+H)$^+$=574.

Anal. ($C_{33}H_{39}N_3O_6$) C: calc. 69.09; found 69.13; H: calc. 6.85; found 6.75; N: calc. 7.32; found 7.42. TLC: $R_f$(10:1 methylene chloride:THF) 0.65. HPLC: retention time 18.7 min.

Step 2.3

1-(4-Biphenylyl)-1-oxo-5(S)-2,5-di[(tert-butoxycarbonyl)amino]-4(S)-hydroxy-6-phenyl-2-azahexane 1.16 g (18.5 mmol) of sodium cyanoborohydride are added at room temperature to a suspension of 9.63 g (16.8 mmol) of 4-(S)-1,4-di[(tert-butoxycarbonyl)-amino]-3(R)-[4-biphenylyl]-carbonyloxy-5-phenyl-1-azapent-1-ene in 90 ml of THF (filtered over basic alox). With stirring at room temperature, a solution of 3.52 g (18.5 mmol) of 4-toluenesulfonic acid monohydrate in 34 ml of THF is added dropwise to the reaction mixture (dropwise addition time: 20 min). After a further 1.5 h, for the purpose of working up, the reaction mixture is diluted with 150 ml of ethyl acetate and washed with 150 ml each of sat. sodium chloride solution, 10% sodium hydrogen carbonate solution and sat. sodium chloride solution. The organic phases are dried over sodium sulfate and concentrated by evaporation and yield the corresponding borate complex in the form of a yellow oil. The oil is dissolved in 130 ml of dioxane, diluted at 0° C. with 80 ml of 1N sodium hydroxide solution and stirred at room temperature for 16 h. The reaction mixture is then poured onto ice, neutralised with 79 ml of 1N hydrochloric acid and extracted three times using 100 ml of methylene chloride each time. The organic extracts are dried over sodium sulfate and concentrated by evaporation. The crude product is purified by chromatography on silica gel (eluant 2%→10% THF in methylene chloride) and yields the title compound in the form of a colorless amorphous solid which is digested in diisopropyl ether. M.p. 125–128° C. $^1$H-NMR (DMSO-$d_6$, 150° C.) δ8.66 (br, 1H), 7.62 (m, 4H); 7.58 (d, J=7.5 Hz, 2H); 7.45 (t, J=7.5 Hz, 2H); 7.38 (m, 1H); 7.26 (m, 4H); 7.17 (m, 1H); 5.72 (d, br, J=10 Hz, 1H); 4.4 (br, 1H); 3.92 (br, 1H); 3.83 (m, 1H); 3.71 (m, 1H); 3.54 (d, br, 1H); 2.92 (dd, J=14, 7 Hz, 1H); 2.80 (dd, J=14, 7 Hz, 1H); 1.32 (s, 9H); 1.29 (s, 9H). FAB MS (M+H)$^+$=576. Anal. ($C_{33}H_{41}N_3O_6$) C: calc. 68.85; found 68.88; H: calc. 7.18; found 7.19; N: calc. 7.30; found 7.31. TLC: $R_f$ (10:1 methylene chloride:THF) 0.58. HPLC: retention time 17.9 min.

EXAMPLE 3

1-(4-(Pyridin-2-yl)phenyl)-5(S)-2,5-di[(tert-butoxycarbonyl)amino]-4(S)-hydroxy-6-phenyl-2-azahexane The preparation is carried out analogously to Example 2 starting from 1-(4-(pyridin-2-yl)-phenyl)-1-oxo-5(S)-2,5-di[(tert-butoxycarbonyl)amino]-4(S)-hydroxy-6-phenyl-2-azahexane by reduction with the borane-THF complex.

The synthesis of the starting material is carried out via the following steps:

Step 3.1

1-(R)-Cyano-2(S)-(N-tert-butoxycarbonylamino)-3-phenylpropyl4-[2-pyridyl]-benzoate (3a) and 1-(S)-cyano-2(S)-(N-tert-butoxycarbonylamino)-3-phenylpropyl 4-[2-pyridyl]-benzoate (3b)

The synthesis is carried out analogously to Step 2.1 starting from Boc-(L)-phenylalaninal and the mixed anhydride 4-(pyridin-2-yl)benzoic acid/isobutyloxyformic acid anhydride.

Step 3.2

4-(S)-1,4-Di[(tert-butoxycarbonyl)amino]-3(R)-[4-(pyridin-2-yl) phenyl]-carbonyloxy-5-phenyl-1-azapent-1-ene The synthesis is carried out analogously to Step 2.2 starting from 1-(R)-cyano-N-2-(S)-(tert-butoxycarbonyl)-3-phenylpropyl 4-[2-pyridyl]-benzoate (3a) and 1-(S)-cyano-N-2-(S)-tert-butoxycarbonyl)-3-phenylpropyl 4-[2-pyridyl]-benzoate (3b) and tert-butyl carbazate.

Step 3.3

1-(4-(Pyridin-2-yl)phenyl)-1-oxo-5(S)-2,5-di-[(tert-butoxycarbonyl)amino-]-4(S)-hydroxy-6-phenyl-2-azahexane The synthesis is carried out starting from 4-(S)-1,4-di[(tert-butoxycarbonyl)amino]-3(R)-[4-(pyridin-2-yl)phenyl]-carbonyloxy-5-phenyl-1-azapent-1-ene by reduction with sodium cyanoborohydride and subsequent reaction with sodium hydroxide solution with acyl migration.

re: Step 3.1: The starting material 4-(pyridin-2-yl)benzoic acid/isobutyloxyformic acid anhydride is prepared as follows:

4-(Pyridin-2-yl)benzoic acid (see Butterworth, Heilbronn and Hey: Arylpyridines, J. Chem. Soc. 1940, 356) is reacted with isobutyl chloroformate.

Alternatively and preferably, the synthesis of the title compound from Example 3 may be carried out as follows:

EXAMPLE 4

1-(4-(Pyridin-2-yl)-phenyl)-5(S)-2,5-di[(tert-butoxycarbonyl)amino]-4(S)-hydroxy-6-phenyl-2-azahexane Under a $N_2$ atmosphere, 2.1 ml (2.1 mmol) of a 1.00M solution of diisobutylaluminium hydride in methylene chloride are slowly added dropwise to an ice-cooled solution of 200 mg (0.347 mmol) of 1-[4-(pyridin-2-yl)phenyl]-1-oxo-5(S)-2,5-di[(tert-butoxycarbonyl)amino]-4(S)-hydroxy-6-phenyl-2-azahexane in 5 ml of THF (foams). After 2 h, 7 ml of ethyl acetate are added and after a further 30 min 70 ml of methanol are added. The reaction mixture is heated to room temperature and stirred for 2 h; 0.5 ml of water and 5 g of sodium sulfate are added and the mixture is stirred for a further 1 h to complete the reaction. The salts are filtered off and the filtrate is concentrated by evaporation. Medium-pressure chromatography ($SiO_2$, hexane/ethyl acetate 3:2→ethyl acetate) yields the title compound: m.p. 184° C.; TLC (hexane/ethyl acetate 1:1): $R_f$=0.26; FAB MS (M+H)$^+$= 563.

The synthesis of the starting material is carried out via the following steps:

Step 4.1

4-(Pyridin-2-yl)-benzoic acid methyl ester

In an autoclave, 24.0 g (150 mmol) of 4-cyanobenzoic acid methyl ester (Fluka, Buchs, Switzerland) in 150 ml of toluene are placed under an acetylene atmosphere, and 0.30 g (1.6 mmol) of cobaltocene (=dicyclopentadienylcobalt; Aldrich, Milwaukee/USA) is added. Then an acetylene pressure of 15 atm is applied, and the mixture is heated to 180° C. and stirred for 12 h. After cooling and release of the pressure, 9.5 g of active carbon are added to the black suspension; the mixture is diluted with 250 ml of toluene, stirred for 30 min, filtered and concentrated by evaporation.

Crystallisation from warm ether by the addition of hexane yields the title compound: m.p. 96° C.; TLC (hexane/ethyl acetate 4:1): $R_f$=0.37; FAB MS (M+H)$^+$=214. Further product can be obtained by column chromatography (SiO$_2$, hexane/ethyl acetate 19:1→4:1) of the mother liquor.
Step 4.2

4-(Pyridin-2-yl)-benzoic acid 12.85 g (60.2 mmol) of 4-(pyridin-2-yl)-benzoic acid methyl ester in 125 ml of methanol and 67 ml of 1N sodium hydroxide solution are stirred at room temperature for 6 h. The resulting solution is partially concentrated by evaporation; the aqueous residue is extracted with ethyl acetate and acidified to pH≈1.5 with 2N HCl solution. The title compound precipitates out and can be filtered off and washed with water: TLC (ethyl acetate): $R_f$=0.35; FAB MS (M+H)$^+$=200.
Step 4.3)

4-(Pyridin-2-yl)-benzoic acid/isobutyloxyformic acid anhydride

With the exclusion of air, 6.0 g (30 mmol) of 4-(pyridin-2-yl)-benzoic acid are suspended at −20° C. in 90 ml of THF, and 9.90 ml (90 mmol) of N-methyl-morpholine and 4.32 ml (33 mmol) of isobutyl chloroformate are added. After 30 min the mixture is filtered and washed with a small amount of cold THF; the filtrate is partially concentrated by evaporation and the residue is diluted with methylene chloride, washed with ice-water and cold brine, dried (Na$_2$SO$_4$) and concentrated by evaporation to yield the title compound: $^1$H-NMR (CDCl$_3$) inter alia 8.75 (m, 1H), 8.16 (AB, J=8, 4H), 7.81 (m, 2H), 7.32 (4-line system, J=5, 1H), 4.16 (d, J=7, 2H), 2.10 (9-line system, J=7, 1H), 1.02 (d, J=7, 6H).
Step 4.4)

1-(R)-Cyano-2(S)-(N-tert-butoxycarbonylamino)-3-phenylpropyl [4-(2-pyridyl)]-benzoate 250 mg (0.9 mmol) of benzyltriethylammonium chloride are added at 0° C. to 2.0 g (30 mmol) of potassium cyanide in 7.5 ml of water and 7.5 ml of methylene chloride. A solution of 6.21 g (24.9 mmol) of Boc-(L)-phenylalaninal in 10 ml of methylene chloride and a solution of ≈30 mmol of 4-(pyridin-2-yl)-benzoic acid/isobutyloxyformic acid anhydride in 10 ml of methylene chloride are simultaneously added dropwise thereto. After 20 min at 0° C., the mixture is stirred at room temperature for a further 4 h and finally diluted with methylene chloride/water. The aqueous phase is separated off and extracted 2× with methylene chloride; the organic phase is washed with 3× water and brine, dried (Na$_2$SO$_4$) and concentrated by evaporation. Column chromatography (SiO$_2$, hexane/ethyl acetate 4:1≈2:1) yields a ≈5:1 mixture of 1-(R)-cyano-2(S)-(N-tert-butoxycarbonylamino)-3-phenylpropyl [4-(2-pyridyl)]-benzoate and 1-(S)-cyano-2(S)-(N-tert-butoxycarbonylamino)-3-phenylpropyl [4-(2-pyridyl)]-benzoate: TLC (hexane/ethyl acetate 4:1): $R_f$=0.11; FAB MS (M+H)$^+$=458; $^1$H-NMR (CDCl$_3$) inter alia 5.66 (d, J=6, ⅚H, 1-(R)-epimer), 5.53 (m, ⅙H, 1-(S)-epimer). Digestion in diisopropyl ether yields diastereoisomerically pure 1-(R)-cyano-2(S)-(N-tert-butoxycarbonylamino)-3-phenylpropyl [4-(2-pyridyl)]-benzoate: m.p. 140–141° C.
Step 4.5)

4-(S)-1,4-Di[(tert-butoxycarbonyl)amino]-3(R)-[4-(pyridin-2-yl) phenyl]-carbonyloxy-5-phenyl-1-azapent-1-ene 2.29 g (5.0 mmol) of 1-(R)-cyano-2(S)-(N-tert-butoxycarbonylamino)-3-phenylpropyl [4-(2-pyridyl)]-benzoate are dissolved in 80 ml of methanol; 900 mg (15 mmol) of acetic acid and 661.5 mg (5 mmol) of tert-butyl carbazate are added and after the addition of 2.3 g of Raney nickel, hydrogenation is carried out. The partially precipitated product is dissolved by the addition of methanol and gentle heating and the catalyst is filtered off and the filtrate is concentrated by evaporation. The residue is taken up in ethyl acetate/sat. NaHCO$_3$ solution; the aqueous phase is separated off and extracted a further 2× with ethyl acetate. The organic phases are washed with brine, dried (Na$_2$SO$_4$) and concentrated by evaporation. Medium-pressure chromatography (SiO$_2$, hexane/ethyl acetate 4:1→ethyl acetate) yields the title compound: m.p. 195–196° C.; TLC (hexane/ethyl acetate 1:1): $R_f$=0.39; FAB MS (M+H)$^+$=575.
Step 4.6)

1-[4-(Pyridin-2-yl)phenyl]-1-oxo-5(S)-2,5-di[(tert-butoxycarbonyl)amino]-4(S)-hydroxy-6-phenyl-2-azahexane Under a N$_2$ atmosphere, 111 mg (85%; 1.5 mmol) of NaCNBH$_3$ are added to a solution of 862 mg (1.5 mmol) of 4-(S)-1,4-di[(tert-butoxycarbonyl)amino]-3(R)-[4-(pyridin-2-yl)phenyl]-carbonyloxy-5-phenyl-1-azapent-1-ene in 10 ml of THF. A solution of 290 mg (1.5 mmol) of p-toluenesulfonic acid in 4 ml of THF is added dropwise thereto. After stirring for 2.5 h, a further 55 mg of NaCNBH$_3$ and 145 mg of p-toluenesulfonic acid in 2 ml of THF are added and the mixture is stirred for a further 2.5 h. The reaction mixture is then poured into 230 ml of a 1% solution of K$_2$B$_4$O$_7$·4H$_2$O in water, stirred overnight to complete the reaction, filtered and washed with water. The residue is taken up in ethyl acetate and the solution is washed with brine, dried (Na$_2$SO$_4$) and concentrated by evaporation {→4-(S)-1,4-di[(tert-butoxycarbonyl)amino]-3(S)-[4-(pyridin-2-yl)phenyl]-carbonyloxy-5-phenyl-1-azapentane: TLC (hexane/ethyl acetate 1:1): $R_f$=0.45}. The resulting foam is dissolved in 25 ml of diethylene glycol dimethyl ether; 250 μl of 7-methyl-1,5,7-triazabicyclo[4.4.0]dec-5-ene (Fluka; Buchs/Switzerland) are added and the mixture is heated at 80° C. for 1.5 h. After concentration by evaporation under a high vacuum, the residue is taken up in ethyl acetate/water; the aqueous phase is separated off and extracted a further 2× with ethyl acetate. The organic phases are washed with brine, dried (Na$_2$SO$_4$) and concentrated by evaporation. Crystallisation from DIPE/hexane yields the title compound: m.p. 104–105° C.; TLC (hexane/ethyl acetate 1:1): $R_f$=0.20; FAB MS (M+H)$^+$=577.

The following Examples 5 to 8 are intended to demonstrate by way of example the pharmaceutical activity, mentioned at the beginning, of a compound obtainable from the title compound from Example 4:

EXAMPLE 5

The title compound from Step 4.6 can then be converted into the pharmacologically active compound indicated below analogously to the following procedure:

1-[4-(Pyridin-2-yl)-phenyl]-4(S)-hydroxy-5(S)-2,5-bis[N-(N-methoxycarbonyl-(L)-tert-leucyl)-amino]-6-phenyl-2-azahexane With the exclusion of moisture, 567 g (3.0 mol) of N-methoxycarbonyl-(L)-tert-leucine (Example 5b)) and 891 g (3.0 mol) of TPTU are introduced into 3 liters of methylene chloride; with ice-cooling, 775 g (6 mol) of Hünig base are added dropwise and the mixture is stirred for 20 min. A suspension of 432 g (1.0 mol) of 1-[4-(pyridin-2- yl)-phenyl]-4(S)-hydroxy-5(S)-2,5-diamino-6-phenyl-2-azahexane trihydrochloride in 3 liters of methylene chloride is then added to the solution and the mixture is stirred at room temperature over-night to complete the reaction. The reaction mixture is washed with 10 liters of water, 10 liters of sat. NaHCO$_3$ solution and 5 liters of brine. The aqueous phases are extracted a further 2× with 5 liters of methylene chloride, and the organic phases are dried (Na$_2$SO$_4$) and concentrated by evaporation. The residue is dissolved in 6 liters of ethyl acetate and filtered through 500 g of silica gel; the column is then washed with 6 liters of ethyl acetate and the product-containing fractions are concentrated by evaporation. Stirring in boiling DIPE/ethanol 49:1 (9 liters; 1 h), cooling and filtration yield the title compound which can be purified further by recrystallisation from ethanol/water (m.p. 207–209° C.).

The starting material is prepared as follows:

5a) 1-[4-(Pyridin-2-yl)-phenyl]-4(S)-hydroxy-5(S)-2,5-diamino-6-phenyl-2-axahexane trihydrochloride A solution of 1465 g (2.6 mol) of 1-[4-(pyridin-2-yl)-phenyl]-4(S)-hydroxy-5(S)-2,5-bis[(tert-butoxycarbonyl)amino]-6-phenyl-2-azahexane (Example 4) in 12 liters of THF and 4 liters of hydrochloric acid (4N in water) is stirred at 50° C. for 4 h. The aqueous phase is separated from the resulting two-phase mixture and concentrated by evaporation in vacuo. The residue is diluted with 4 liters of ethanol, concentrated by evaporation, diluted with 4 liters of ethanol/toluene 1:1, concentrated by evaporation, diluted with 4 liters of ethanol and again concentrated by evaporation. Stirring in 9 liters of DIPE and filtration yield the title compound ($^1$H-NMR (CD$_3$OD; 200 MHz) inter alia: 8.78/d, J=5 (1H); 8.72/d×t, J=2.5 and 7.5 (1H); 8.35/d, J=7.5 (1H); 8.1/d×d, J=each 7.5 (1H); 8.02 and 7.72/each d, J=9 (2×2H); 7.45–7.15/m (5H); 4.27 and 4.15/each d, J=12.5 (2×2H)).

5b) N-(Methoxycarbonyl)-(L)-tert-leucine 23.5 ml (305 mmol) of methyl chloroformate are added over a period of 20 min to a solution of 20 g (152 mmol) of (L)-tert-leucine (=2(S)-amino-3,3-dimethyl-butyric acid= (L)-α-tert-butylglycine; Fluka, Buchs/Switzerland) in a mixture of 252 ml (504 mmol) of 2N aqueous sodium hydroxide solution and 80 ml of dioxane, and the reaction solution is heated at 60° C. for 14 h. After cooling to room temperature, the reaction solution is washed 2× with methylene chloride. The aqueous phase is acidified to pH 2 with 4N aqueous hydrochloric acid and extracted three times with ethyl acetate. The organic extracts are combined, dried (Na$_2$SO$_4$) and concentrated by evaporation, the product beginning to solidify. Digestion of the solidified solid with hexane yields the title compound in the form of a white powder. M.p. 106–108° C.

EXAMPLE 6

Inhibitory action of the title compound from Example 5 on HIV-1-protease

The inhibitory action of 1-[4-(pyridin-2-yl)-phenyl]-4(S)-hydroxy-5(S)-2,5-bis[N-(N-methoxy-carbonyl-(L)-tert-leucyl)amino]-6-phenyl-2-azahexane on the proteolytic activity of HIV-1-protease can be demonstrated by known procedures (see A. D. Richards et al, J. Biol. Chem. 265 (14), 7733–7736 (1990)). In that procedure the inhibition of the action of HIV-1- protease (preparation: see S. Billich et al., J. Biol. Chem. 263 (34), 17905–17908 (1990)) is measured in the presence of the icosapeptide RRSNQVSQNYPIVQ-NIQGRR (a synthetic substrate of HIV-1-protease, prepared by peptide synthesis in accordance with known procedures (see J. Schneider et al., Cell 54, 363–368 (1988)), which contains as substrate analogue one of the cleavage sites of the gag-precursor protein (natural substrate of HIV-1-protease). That substrate and its cleavage products are analysed by high performance liquid chromatography (HPLC).

The test compound is dissolved in dimethyl sulfoxide. The enzymatic test is carried out by adding suitable dilutions of the inhibitor in 20 mM β-morpholinoethanesulfonic acid (MES) buffer pH 6.0 to the test mixture. That mixture consists of the above-mentioned icosapeptide (122 μM) in 20 mM MES buffer pH 6.0. 100 μl are used per test batch. The reaction is started by the addition of 10 ml of HIV-1-protease solution and is stopped after one hour's incubation at 37° C. by the addition of 10 μl of 0.3M HClO$_4$. After centrifugation of the sample at 10000×g for 5 minutes, 20 μl of the resulting supernatant are applied to a 125×4.6 mm Nucleosil® Cl8-5 μ HPLC column (reversed phase material supplied by Macherey & Nagel, Düren, FRG, based on silica gel that has been charged with C$_{18}$alkyl chains). The uncleaved icosapeptide and its cleavage products are eluted from the column by means of the following gradient: 100% eluant 1→50% eluant 1+50% eluant 2 (eluant 1:10% acetonitrile, 90% H$_2$O, 0.1% trifluoroacetic acid (TFA); eluant 2:75% acetonitrile, 25% H$_2$O, 0.08% TFA) over 15 minutes, throughflow rate 1 ml/min. The quantification of the eluted peptide fragments is carried out by measuring the peak height of the cleavage product at 215 nm.

The following IC$_{50}$ (concentration at which half the maximum inhibition of HIV-1-protease is found) is obtained: 0.026 μM.

EXAMPLE 7

Inhibitory action of 1-[4-(pyridin-2-yl)-phenyl]-4(S)-hydroxy-5(S)-2,5-bis[N-(N-methoxycarbonyl-(L)-tert-leucyl)amino]-6-phenyl-2-azahexane on virus replication In a further test it can be shown that the title compound from Example 5 protects cells normally infected by HIV from such an infection or at least slows down such an infection. For this test, MT-2 cells infected with HIV-1/MN are used. MT-2 cells have been transformed with HTLV-1 (a virus causing leukaemia) and are a continuous producer thereof; they are therefore especially sensitive to the cytopathogenic effect of HIV. MT-2 cells can be obtained via the AIDS Research and Reference Reagent Program, Division of AIDS, NIAID, NIH from Dr. Douglas Richman (see J. Biol. Chem. 263, 5870–5875 (1988) and also Science 229, 563–566 (1985)). The MT-2 cells are cultured in RPMI 1640 medium (Gibco, Scotland; RPMI comprises an amino acid mixture without glutamine) supplemented with 10% heat-inactivated foetal calf serum, glutamine and standard antibiotics. In all cases the cells, and also the virus stock solution used for the infection (HIV-1/MN), are free of mycoplasmas. The virus stock solution is prepared as a cell culture supernatant of the permanently infected cell line H9/HIV-1/MN, which can likewise be obtained via the AIDS Research and Reference Program, Division of AIDS, NIAID, NIH from Dr. Robert Gallo (see also Science 224, 500–503 (1984) and Science 226, 1165–1170 (1984)). The titre of the HIV-1/MN virus stock solution (determined by titration onto MT-2 cells) is 4.2×10$^5$ TClD50/ml (TClD50=Tissue Culture Infective Dose=dose that infects 50% of the MT-2 cells). In order to measure the infection-inhibiting action of the title compound from Example 5, 50 μl of the test compound in question in culture medium and 2800 TClD50 of HIV-1/MN in 100 μl of culture medium are added to 2×10$^4$ exponentially growing MT-2 cells which have been added in 50 μl of culture medium to 96-well microtitre plates (round-bottomed wells). After 4 days' incubation (at 37° C., 5% $CO_2$) a 10 µl sample of the supernatant is taken from each well, transferred to a further 96-well microtitre plate and (if necessary) stored at −20° C. In order to measure the activity of the virus-associated reverse transcriptase, 30 µl of reverse transcriptase (RT) cocktail are added to each sample. The reverse transcriptase cocktail consists of 50 mM Tris (α,α, α-tris-(hydroxymethyl)methylamine, Ultra pur, Merck, Germany) pH 7.8; 75 mM KCl, 2 mM dithiothreitol, 5 mM $MgCl_2$; 0.1% Nonidet P-40 (detergent, Sigma, Switzerland), 0.8 mM EDTA, 10 µg/ml Poly-A (Pharmacia, Uppsala, Sweden) and 0.16 µg/ml oligo(T) (=pdT(12–18), Pharmacia, Uppsala, Sweden) as "template primer"—if desired, the mixture is filtered through a 0.45 µm Acrodisc filter (Gelman Sciences Inc., Ann Arbor, USA). It is stored at −20° C. Prior to the test, 0.1% (v/v) [alpha-$^{32}$P]dTTP is added to aliquots of the solution in order to establish a radioactivity of 10 µCl/ml.

After mixing, the plate is incubated for 2 h at 37° C. 5 µl of the reaction mixture are transferred to DE81 paper (Whatman, one filter per well). The dried filters are washed three times for 5 minutes with 300 mM NaCl/25 mM trisodium citrate and then once with ethanol and again dried in the air. The radioactivity on the filters is measured in a Matrix Packard 96-well counter (Packard, Zürich, Switzerland). The $ED_{90}$ values are calculated and are defined as the concentration of the test compound that reduces the RT activity by 90% in comparison with a control without test compound.

The title compound from Example 5 here exhibits an $ED_{90}$, that is to say a 90% inhibition of virus replication, of 0.003 µM.

Accordingly, the compounds of formula I are suitable for the highly effective slowing down of the replication of HIV-1 in cell cultures.

EXAMPLE 8
Plasma levels in mice in the case of oral administration of 1-[4-(pyridin-2-yl)-phenyl]-4(S)-hydroxy-5(S)-2,5-bis[N-(N-methoxycarbonyl-(L)-tert-leucyl)amino]-6-phenyl-2-azahexane In order to determine its pharmacokinetics, the title compound from Example 5 is dissolved in dimethyl sulfoxide (DMSO) in a concentration of 240 mg/ml. The resulting solution is diluted 1:20 (v/v) with 20% (w/v) aqueous hydroxypropyl-β-cyclodextrin solution in order to obtain a concentration of the test compound of 12 mg/ml. The resulting solution is treated briefly with ultrasound and administered orally to female BALB/c mice (Bomholtgarden, Copenhagen, Denmark) by artificial tube feeding at a dose of 120 mg/kg. At fixed times (for example 30, 60, 90, 120 min) after administration, mice are sacrificed and the plasma stored in heparinised test tubes. The blood is centrifuged (12000×g, 5 min) and the plasma removed. The plasma is deproteinised by the addition of an equal volume of acetonitrile. The mixture is mixed using a vortex mixer and left to stand at room temperature for 20 to 30 minutes. The precipitate is pelleted by centrifugation (12000×g, 5 min), and the concentration of the test compound is determined by reversed phase high performance liquid chromatography (HPLC).

The HPLC analysis of the samples obtained in accordance with the method described above is carried out on a 125×4.6 mm Nucleosil® $C_{18}$ column (reversed phase material supplied by Macherey & Nagel, Düren, Germany, based on silica gel derivatised with hydrocarbon radicals having 18 carbon atoms), using a 2 cm long preliminary column containing the same column material. The test is carried out with the following linear acetonitrile/water gradient (in each case in the presence of 0.05% trifluoroacetic acid): 20% acetonitrile to 100% acetonitrile over 20 min; then 5 min 100% acetonitrile; then returning to the initial conditions over 1 min and 4 min re-equilibration. The flow rate is 1 ml/min. Under those conditions the compound of formula I from Example 1, for example, has a retention time of about 15.5 minutes, and its detection limit is 0.1–0.2 µM. The test compound is detected by UV absorption measurement at 255 nm. Peaks are identified by the retention time and the UV spectrum between 205 and 400 nm. The concentrations are determined by the external standard method; the peak heights are obtained for determining the concentrations by comparison with standard curves. The standard curves are obtained by analogous HPLC analysis of mouse plasma that contains known concentrations of the test compound and that has been worked up in accordance with the method described above.

In that experiment, the title compound from Example 5 produces plasma concentrations far above the $ED_{90}$ determined above in the cell experiment:

| plasma level (µM) of title compound from Example 5 | |
| --- | --- |
| 30 min | 90 min after administration |
| 21.83 | 31.76 |

EXAMPLE 9

Analogously to one of the processes given above and in Examples 1 to 4, it is possible to prepare the following intermediates for the pharmaceutically active compounds given afterwards in parenthesis:

a) 1-[4-(2-Methyl-2H-tetrazol-5-yl)-phenyl]-4(S)-hydroxy-5(S)-2,5-bis[(tert-butyloxycarbonyl)-amino]-6-phenyl-2-azahexane (for the preparation analogously to Example 5 of 1-[4-(2-methyl-2H-tetrazol-5-yl)-phenyl]-4(S)-hydroxy-5(S)-2,5-bis[N-(N-methoxycarbonyl-(L)-tert-leucyl)amino]-6-phenyl-2-axahexane, $IC_{50}$ in the inhibition of HIV-protease analogous to Example 5: 0.051 µM).

b) 1-[4-(Thiazol-2-yl)-phenyl]-4(S)-hydroxy-5(S)-2,5-bis[(tert-butoxycarbonyl)amino]-6-phenyl-2-azahexane (for the preparation analogously to Example 5 of 1-[4-(thiazol-2-yl)-phenyl]-4(S)-hydroxy-5(S)-2,5-bis[N-(N-methoxycarbonyl-(L)-tert-leucyl)amino]-6-phenyl-2-azahexane, $IC_{50}$ in the inhibition of HIV-protease analogous to Example 5: 0.033 µM).

What is claimed is:

1. A process for the preparation of a compound of formula I

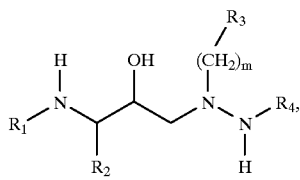

wherein $R_1$ is hydrogen or an amino-protecting group, $R_2$ is unsubstituted or substituted alkyl, $R_3$ is hydrogen, aryl, heterocyclyl, unsubstituted or substituted alkyl or unsubstituted or substituted cycloalkyl, $R_4$, independently of $R_1$, is hydrogen or an amino-protecting group and m is a number from 1 to 7;

and wherein further suitable protecting groups for functional groups may be present;

or of salts thereof where salt-forming groups are present;

wherein the preparation is carried out by reduction of an oxo compound of formula II

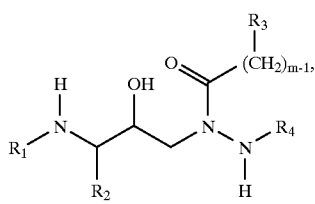

wherein $R_1$, $R_2$, $R_3$, $R_4$ and m are as defined for compounds of formula I, and wherein further suitable protecting groups for functional groups may be present;

which compound is in turn prepared by hydrogenation with a suitable complex hydride or with hydrogen in the presence of a suitable catalyst and acyl migration starting from a hydrazone of formula II

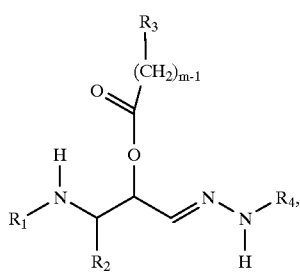

wherein $R_1$, $R_2$, $R_3$, $R_4$ and m are as defined for compounds of formula I, and wherein further suitable protecting groups for functional groups may be present;

which compound is in turn obtained from a nitrile of formula IV

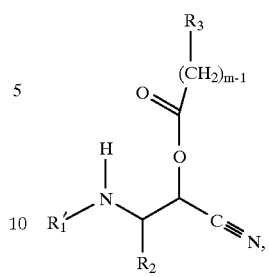

wherein $R_1'$ is an amino-protecting group and $R_2$, $R_3$ and m are as defined for compounds of formula I, by means of selective catalytic hydrogenation and reaction with a hydrazine derivative of formula VI

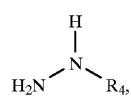

wherein $R_4$ is as defined for a compound of formula I, and wherein further suitable protecting groups for functional groups may be present;

the hydrazine derivative being added during the selective catalytic hydrogenation or being reacted with the resulting imino compound of formula V only when the catalytic hydrogenation is complete, the compound of formula IV being prepared from an aldehyde of formula VII

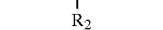

wherein $R_1'$ is an amino-protecting group, and wherein further suitable protecting groups for functional groups may be present;

by reaction with a reactive derivative of a carboxylic acid of formula VIII

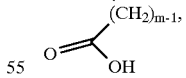

wherein $R_3$ and m are as defined for compounds of formula I, and wherein further suitable protecting groups for functional groups may be present; in the presence of a cyanide salt;

it being possible for the compounds of formulae II to VIII to be used in free form or, where salt-forming groups are present, in the form of their salts.

2. A process according to claim 1 for the preparation of a compound of formula I'

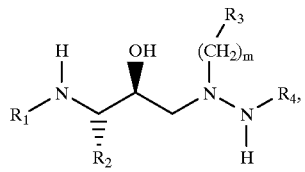

(I')

wherein
- $R_1$ is hydrogen, 1-[1-adamantyl]-1-methylethoxycarbonyl, isobornyloxycarbonyl, cyclopentyloxycarbonyl,- 5,5-dimethyl-3-oxo-cyclohexen-1-yl or tert-lower alkoxycarbonyl;
- $R_2$ is lower alkyl that is unsubstituted or substituted by phenyl that is unsubstituted or substituted by one or more substituent(s) selected from halogen, nitro, lower alkoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3-C_8$cycloalkyl, phenyl, phenyl-lower alkyl, carboxy, sulfo or by lower alkyl; or by $C_3-C_8$cycloalkyl;
- $R_3$ is phenyl that is unsubstituted or substituted by one or more substituent(s) selected from halogen, nitro, lower alkoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3-C_8$cycloalkyl, phenyl, phenyl-lower alkyl, carboxy, sulfo or by lower alkyl; or is $C_3-C_8$cycloalkyl;
- $R_4$, independently of $R_1$, is hydrogen or one of the radicals mentioned for $R_1$; and
- m is from 1 to 4;

or of a salt thereof where a salt-forming group is present; wherein the preparation is carried out by reduction of an oxo compound of formula II'

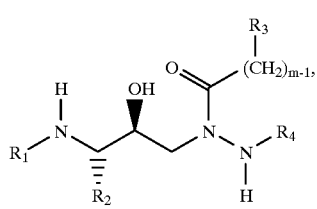

(II')

wherein $R_1$, $R_2$, $R_3$, $R_4$ and m are as defined for compounds of formula I',
which compound is in turn prepared by hydrogenation with a suitable complex hydride and acyl migration starting from a hydrazone of formula III'

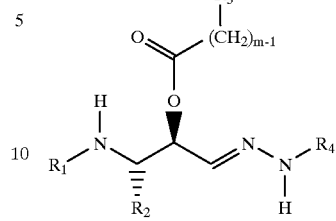

(III')

wherein $R_1$, $R_2$, $R_3$, $R_4$ and m are as defined for compounds of formula I',
which is in turn obtained starting from a nitrile of formula IV'

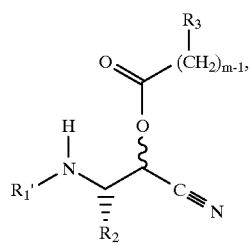

(IV')

wherein $R_1'$ has one of the definitions given for $R_1$ in formula I' with the exception of hydrogen and $R_2$, $R_3$ and m are as defined for compounds of formula I', by means of selective catalytic hydrogenation and by reaction with a hydrazine derivative of formula VI

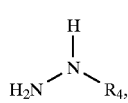

(VI)

wherein $R_4$ is as defined for a compound of formula I';
the hydrazine derivative being added during the selective catalytic hydrogenation,
the compound of formula IV' being prepared from an aldehyde of formula VII'

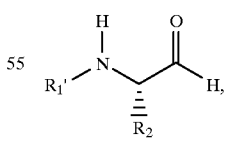

(VII')

wherein $R_1'$ has one of the definitions mentioned for $R_1$ under formula I' with the exception of hydrogen;
by reaction with a reactive derivative of a carboxylic acid, of formula IX

wherein $R_3$ and m are as defined for compounds of formula I' and and wherein X is halogen or a radical of a carboxylic acid of formula VIII itself bonded via an oxygen atom, lower alkanoyloxy or lower alkoxycarbonyloxy; in the presence of a cyanide salt;

it being possible for the compounds of formulae II' to VIII' to be used in free form or, where salt-forming groups are present, in the form of their salts;

wherein the reduction of an oxo compound of formula II' is carried out using borane/tetrahydrofuran, borane/dimethyl sulfide, tetra(n-butyl)ammonium borohydride, lithium borohydride, sodium borohydride, potassium borohydride, lithium triethylborohydride, potassium tri(sec-butyl)borohydride, potassium tri(siamyl)borohydride, lithium tri (sec-butyl)borohydride, lithium tri(siamyl)borohydride, sodium tri(sec-butyl) borohydride, lithium aminoborohydride, sodium dimethylaminoborohydride, lithium diethylaminoborohydride, lithium di-n-propyl-aminoborohydride, lithium diisopropylaminoborohydride, lithium 1-azaheptano-borohydride, lithium pyrrolidino-borohydride, lithium morpholino-borohydride, lithium piperidino-borohydride, lithium (N-ethyl-N-phenyl-amino) borohydride, sodium bis(2-methoxyethoxy)aluminium hydride, lithium aluminium hydride, lithium tri (methoxy)aluminium hydride, diisobutyl-aluminium hydride or lithium tri(tert-butoxy)aluminium hydride, in an ether, a halogenated hydrocarbon, an ester, an alcohol, or mixtures of some or all of the solvents mentioned, at temperatures of from −10° to 80° C.;

for the hydrogenation with a suitable complex hydride and acyl migration starting from a hydrazone of formula III' there is used as the complex hydride an alkali metal cyanoborohydride in the presence of sulfuric acid, phosphoric acid, hydrochloric acid, hydrobromic acid or hydrofluoric acid, an alkanesulfonic acid or an aromatic sulfonic acid, the reaction being carried out in ethers in the presence of water or in the absence thereof, at temperatures of from 0° to 80° C.; and the resulting borate complex is used further after being worked up or directly in situ; and the acyl migration of the radical $R_3-(CH_2)_{m-1}-C(=O)$—from the oxygen atom in formula II' to the hydrazine nitrogen atom in formula II' is carried out in the presence of an aqueous base in the absence or presence of an ether at temperatures of from −10° to 60° C., especially from 0° to 30° C.;

the selective catalytic hydrogenation starting from a nitrile of formula IV' and reaction with a hydrazine derivative of formula VI, the hydrazine derivative being added during the selective catalytic hydrogenation, are carried out using cobalt or nickel catalysts, which are used in free form or bonded to active carbon, aluminium oxide or barium sulfate, in the presence of molecular hydrogen, and an aliphatic monocarboxylic acid having from 1 to 18 carbon atoms, the acid and the hydrazine derivative of formula VI advantageously being used in at least equimolar amounts, based on the compound of formula IV', with the hydrazine derivative being used in an equimolar to twice the molar amount and the acid in an equimolar to four times the molar amount, in the presence or absence of alcohols, aliphatic or cyclic ethers or cyclic or aliphatic amides or mixtures of the solvents mentioned with water; at temperatures of from 0° to 150° C.; at pressures from normal pressure to a pressure of up to 10 bar; and for the reaction of an aldehyde of formula VII' with a reactive derivative of a carboxylic acid of formula IX in the presence of a cyanide salt there is used an alkali metal cyanide; and the reaction is carried out under phase transfer conditions in the presence of a tricaprylmethylammonium halide, tetraalkylammonium halide, trialkyl-aryl-lower alkyl-ammonium halide, benzylcinchoninium halide, benzylcinchonidinium halide or benzylquininium halide, in mixtures of halogenated hydrocarbons with water or mixtures of aliphatic ethers with water, or cyclic ether/water mixtures, at temperatures of from −20 to 50° C.

3. A process according to claim 1 for the preparation of a compound of formula I'

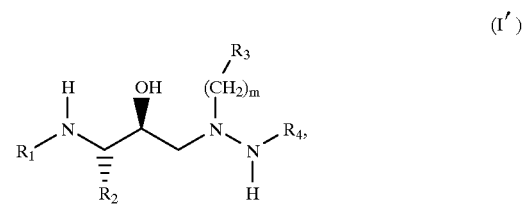

wherein $R_1$ is hydrogen, 1-[1-adamantyl]-1-methylethoxycarbonyl, isobornyloxycarbonyl, cyclopentyl-oxycarbonyl, 5,5-dimethyl-3-oxo-cyclohexen-1-yl or tert-lower alkoxycarbonyl;

$R_2$ is lower alkyl that is unsubstituted or substituted by phenyl that is unsubstituted or substituted by one or more substituent(s) selected from halogen, nitro, lower alkoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro [2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3-C_8$cycloalkyl, phenyl, phenyl-lower alkyl, carboxy, sulfo or by lower alkyl; or by $C_3-C_8$cycloalkyl;

$R_3$ is phenyl that is unsubstituted or substituted by one or more substituent(s) selected from halogen, nitro, lower alkoxy, hydroxy, phenyl and heterocyclyl selected from pyrrolyl, imidazolyl, tetrazolyl, pyridyl, piperidyl, thiazolyl, isothiazolyl, oxazolyl, isoxazolyl, benzisoxazolyl, furanyl, thienyl, tetrahydrofuranyl, tetrahydrothienyl and tetrahydro[2H]pyranyl, with heterocyclyl being unsubstituted or substituted by hydroxy, halogen, oxo, lower alkylimino, amino, lower alkylamino, di-lower alkylamino, lower alkoxy, halo-lower alkyl, $C_3-C_8$cycloalkyl, phenyl, phenyl-lower alkyl, carboxy, sulfo or by lower alkyl; or is $C_3-C_8$cycloalkyl;

$R_4$, independently of $R_1$, is hydrogen or one of the radicals mentioned for $R_1$; and m is from 1 to 4;

or of a salt thereof where a salt-forming group is present; wherein the preparation is carried out by reduction of an oxo compound of formula II'

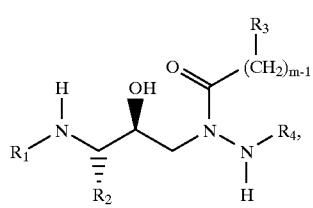
(II')

wherein $R_1$, $R_2$, $R_3$, $R_4$ and m are as defined for compounds of formula I', which compound is in turn prepared by hydrogenation with a suitable complex hydride and acyl migration starting from a hydrazone of formula III'

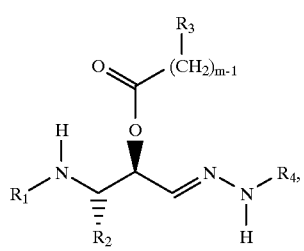
(III')

wherein $R_1$, $R_2$, $R_3$, $R_4$ and m are as defined for compounds of formula I', which is in turn obtained starting from a nitrile of formula IV'

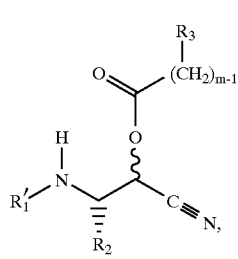
(IV')

wherein $R_1'$ has one of the definitions given for $R_1$ in formula I' with the exception of hydrogen and $R_2$, $R_3$ and m are as defined for compounds of formula I', by means of selective catalytic hydrogenation and by reaction with a hydrazine derivative of formula VI

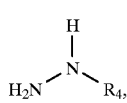
(VI)

wherein $R_4$ is as defined for a compound of formula I'; the hydrazine derivative being added during the selective catalytic hydrogenation, the compound of formula IV' being prepared from an aldehyde of formula VII'

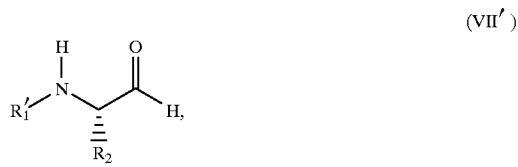
(VII')

wherein $R_1'$ has one of the definitions mentioned for $R_1$ under formula I' with the exception of hydrogen;

by reaction with a reactive derivative of a carboxylic acid of formula IX

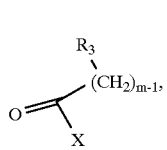
(IX)

wherein $R_3$ and m are as defined for compounds of formula I' and wherein X is halogen or a radical of a carboxylic acid of formula VIII itself bonded via an oxygen atom, lower alkanoyloxy or lower alkoxycarbonyloxy; in the presence of a cyanide salt;

it being possible for the compounds of formulae II' to VIII' to be used in free form or, where salt-forming groups are present, in the form of their salts;

wherein the reduction of an oxo compound of formula II' is carried out using borane/tetrahydrofuran, borane/dimethyl sulfide, tetra(n-butyl)ammonium borohydride, lithium borohydride, sodium borohydride, potassium borohydride, lithium triethylborohydride, potassium tri (sec-butyl)borohydride, potassium tri (siamyl) borohydride, lithium tri (sec-butyl) borohydride, lithium tri(siamyl)borohydride, sodium tri(sec-butyl) borohydride, lithium aminoborohydride, sodium dimethylaminoborohydride, lithium diethylaminoborohydride, lithium di-n-propyl-aminoborohydride, lithium diisopropylaminoborohydride, lithium 1-azaheptano-borohydride, lithium pyrrolidino-borohydride, lithium morpholinoborohydride, lithium piperidino-borohydride, lithium (N-ethyl-N-phenyl-amino)borohydride, sodium bis(2-methoxyethoxy)aluminium hydride, lithium aluminium hydride, lithium tri(methoxy)aluminium hydride, diisobutyl-aluminium hydride or lithium tri (tert-butoxy)aluminium hydride, in ethers or halogenated hydrocarbons, at temperatures of from $-10°$ to $80°$ C.;

for the hydrogenation with a suitable complex hydride and acyl migration starting from a hydrazone of formula III' there is used as the complex hydride an alkali metal cyanoborohydride in the presence of sulfuric acid, phosphoric acid, hydrochloric acid, hydrobromic acid or hydrofluoric acid, an alkanesulfonic acid or an aromatic sulfonic acid, the reaction being carried out in ethers in the presence of water or in the absence thereof, at temperatures of from $0°$ to $80°$ C.; and the resulting borate complex is used further after being worked up or directly in situ; and the acyl migration of the radical $R_3$—$(CH_2)_{m-1}$—C(=O)— from the oxygen atom in formula III' to the hydrazine nitrogen atom in formula II' is carried out in the presence of an aqueous base in the absence or presence of an ether at temperatures of from −10° to 60° C., especially from 0° to 30° C.;

the selective catalytic hydrogenation starting from a nitrile of formula IV' and reaction with a hydrazine derivative of formula VI, the hydrazine derivative being added during the selective catalytic hydrogenation, are carried out using cobalt or nickel catalysts, which are used in free form or bonded to active carbon, aluminium oxide or barium sulfate, in the presence of molecular hydrogen, and an aliphatic monocarboxylic acid having from 1 to 18 carbon atoms, the acid and the hydrazine derivative of formula VI advantageously being used in at least equimolar amounts, based on the compound of formula IV', with the hydrazine derivative being used in an equimolar to twice the molar amount and the acid in an equimolar to four times the molar amount, in the presence or absence of alcohols, aliphatic or cyclic ethers or cyclic or aliphatic amides or mixtures of the solvents mentioned with water; at temperatures of from 0° to 150° C.; at pressures from normal pressure to a pressure of up to 10 bar; and for the reaction of an aldehyde of formula VII' with a reactive derivative of a carboxylic acid of formula IX in the presence of a cyanide salt there is used an alkali metal cyanide; and the reaction is carried out under phase transfer conditions in the presence of a tricaprylmethylammonium halide, tetraalkylammonium halide, trialkyl-aryl-lower alkylammonium halide, benzylcinchoninium halide, benzylcinchonidinium halide or benzylquininium halide, in mixtures of halogenated hydrocarbons with water or mixtures of aliphatic ethers with water, or cyclic ether/water mixtures, at temperatures of from −20° to 50° C.

4. A process according to claim 1 for the preparation of a compound of formula I wherein $R_1$ is tert-butoxycarbonyl, $R_2$ is phenylmethyl, $R_3$ is 4-biphenylyl, $R_4$ is tert-butoxycarbonyl and m is 1 that is carried out starting from appropriately substituted starting materials.

5. A process according to claim 1 for the preparation of a compound of formula I wherein $R_1$ is tert-butoxycarbonyl, $R_2$ is phenylmethyl, $R_3$ is phenyl, $R_4$ is tert-butoxycarbonyl and m is 1 that is carried out starting from appropriately substituted starting materials.

6. A process according to claim 1 for the preparation of a compound of formula I wherein $R_1$ is tert-butoxycarbonyl, $R_2$ is phenylmethyl, $R_3$ is 4-(pyridin2-yl)phenyl, $R_4$ is tert-butoxycarbonyl and m is 1, or of a salt thereof, that is carried out starting from appropriately substituted starting materials.

* * * * *

UNITED STATES PATENT AND TRADEMARK OFFICE
CERTIFICATE OF CORRECTION

PATENT NO. : 5,912,352
DATED : JUNE 15, 1999
INVENTOR(S) : ALEXANDER FÄSSLER ET AL.

It is certified that error appears in the above-identified patent and that said Letters Patent is hereby corrected as shown below:

Column 39, in Claim 1, line 48 should read:

-- starting from a hydrazone of formula III --.

Column 43, in claim 2, line 53 should read:

-- atom in formula III' to the hydrazine nitrogen atom in --.

Signed and Sealed this

Twenty-ninth Day of February, 2000

Attest:

Q. TODD DICKINSON

Attesting Officer

Commissioner of Patents and Trademarks